(12) United States Patent
Müller et al.

(10) Patent No.: US 11,904,051 B2
(45) Date of Patent: Feb. 20, 2024

(54) SHEAR STRESS SENSITIVE LIPOSOMES

(71) Applicants: Universität Basel, Basel (CH); Universität Freiburg, Fribourg (CH)

(72) Inventors: Bert Müller, Embrach (CH); Andreas Zumbühl, Bern (CH); Thomas Pfohl, Basel (CH); Dennis Müller, Buchs (CH); Frederik Neuhaus, Arnsberg-Neheim (DE); Radu Tanasescu, Basel (CH); Till Saxer, Beaumont (FR); Marzia Buscema, Catania (IT); Sofiya Matviykiv, Lviv (UA); Gabriela Gerganova, Sofia (BG)

(73) Assignees: Universität Basel, Basel (CH); Universität Freiburg, Fribourg (CH)

( * ) Notice: Subject to any disclaimer, the term of this patent is extended or adjusted under 35 U.S.C. 154(b) by 79 days.

(21) Appl. No.: 16/966,626

(22) PCT Filed: Jan. 31, 2019

(86) PCT No.: PCT/EP2019/052412
§ 371 (c)(1),
(2) Date: Jul. 31, 2020

(87) PCT Pub. No.: WO2019/149836
PCT Pub. Date: Aug. 8, 2019

(65) Prior Publication Data
US 2021/0030676 A1    Feb. 4, 2021

(30) Foreign Application Priority Data

Jan. 31, 2018 (EP) ..................... 18154352
Jun. 21, 2018 (EP) ..................... 18179147

(51) Int. Cl.
*A61K 9/127* (2006.01)
*A61K 47/24* (2006.01)
*A61K 47/44* (2017.01)

(52) U.S. Cl.
CPC ............ *A61K 9/127* (2013.01); *A61K 47/24* (2013.01); *A61K 47/44* (2013.01)

(58) Field of Classification Search
None
See application file for complete search history.

(56) References Cited

U.S. PATENT DOCUMENTS 10,004,688 B2    6/2018  Barenholz et al.

FOREIGN PATENT DOCUMENTS

| CN | 106659795 A1 | 5/2017 | |
|----|--------------|--------|---|
| WO | 2012/119781 A2 | 9/2012 | |
| WO | WO-2012119781 A2 * | 9/2012 | ........... A61K 31/688 |

OTHER PUBLICATIONS

M. Holme et al., "Shear-stress sensitive lenticular vesicles for targeted drug delivery", Nature Nanotechnology, vol. 7, No. 8, Jun. 10, 2012, See International Search.
I. Fedotenko et al., "The synthesis of 1,3-diamidophospholipds", Tetrahedron Letters, Elsevier, Amsterdam, NL, vol. 51, No. 41, Jul. 23, 2010, See International Search.
International Search Corresponding to PCT/EP2019/052412 dated Apr. 29, 2019.
Written Opinion Corresponding to PCT/EP2019/052412 dated Apr. 29, 2019.
M. Buscema et al., "Immunological response to nitroglycerin-loaded shear-responsive liposomes in vitro and in vivo", Journal of Controlled Release, vol. 264, pp. 14-23, Oct. 28, 2017.
A. Weinberger et al., "Bilayer properties of 1,3-diamidophospholipids", Langmuir, vol. 31, No. 6, pp. 1879-1884, Feb. 17, 2015.
Examination Report corresponding to Japanese Application 2020-563807 dated Sep. 13, 2022.
Chinese Office Action Corresponding to 201980010892.4 dated Sep. 27, 2022.
Chinese Office Action Corresponding to CN201980010892.4 dated Jan. 6, 2022.

* cited by examiner

*Primary Examiner* — Celeste A Roney
(74) *Attorney, Agent, or Firm* — Finch & Maloney PLLC

(57) ABSTRACT

A liposome vesicle comprising a membrane consisting of 1,3-diheptadecanamidopropan-2-yl(2-(trimethylammonio)ethyl)phosphate surrounding a volume comprising a pharmaceutical drug or contrast agent. The vesicle is mechano-sensitive at body temperature and at physiologically or pathophysiologically relevant shear stress.

17 Claims, 20 Drawing Sheets

SHEAR STRESS SENSITIVE LIPOSOMES

The present invention relates to the new diamidophospholipid 1,3-diheptadecanamidopropan-2-yl (2-(trimethylammonio) ethyl)phosphate (4) and to monolayer membranes, bilayer membranes and mechanoresponsive vesicles formed thereof. The mechanoresponsive vesicles may be used as drug delivery vehicles that allow drug targeting at human body temperature.

DESCRIPTION

The emerging field of mechanoresponsive drug delivery seeks to harness differences in the physical properties of a healthy tissue versus diseased tissue as triggers for drug targeting. Shear force is a trigger in blood vessels. Following Murray's law, shear force is balanced below 1.5 Pa throughout the entire vascular system in order to minimize the work needed to transport blood in the body. At the site of a stenosis, the shear force is at least ten times higher and this change in force can be used to activate drug release from either nanoparticle aggregates or lenticular vesicles.

Compared to the natural phospholipid 1,2-dipalmitoyl-sn-glycero-3-phosphocholine (DPPC; see formula 1 in FIG. 1) the 1,3-palmitoylamido-1,3-deoxy-sn-glycero-2-phosphatidylcholine (Pad-PC-Pad; see formula 2 in FIG. 1) features two major differences: i) the fatty acyl esters are replaced with amide moieties capable of forming intermolecular H-bonding networks and ii) the non-natural 1,3-arrangement spaces the tails apart, leading to an interdigitated bilayer membrane (FIG. 1). The combination of these two effects leads to constrictions on the vesicle geometry, and lenticular or d-form shaped vesicles are formed. The vesicles are tight when left untouched but release their cargo when they are mechanically stimulated, e.g. by shaking. In other words, the vesicles are mechanoresponsive.

Self-assembled vesicles containing artificial phospholipid 1,3-palmitoylamido-1,3-deoxy-sn-glycero-2-phosphatidylcholine are nontoxic, and generally do not activate the complement system. Therefore, vesicles comprising 1,3-palmitoylamido-1,3-deoxy-sn-glycero-2-phosphatidylcholine can be candidates for mechanoresponsive vesicular drug delivery. However, the main phase transition temperature ($T_m$) of 1,3-palmitoylamido-1,3-deoxy-sn-glycero-2-phosphatidylcholine lies at 37° C., and heating the vesicles to this temperature leads to an immediate full release of any vesicle-entrapped cargo due to the leakiness of a liquid-crystalline membrane. It is therefore desirable to increase the $T_m$ of the membrane while maintaining the mechanosensitivity.

Based on the above-mentioned state of the art, the objective of the present invention is to provide improved vesicles for mechanoresponsive drug delivery. These objectives are attained by the claims of the present specification.

Terms and Definitions

The term faceted form in the context of the present specification relates to a vesicle that is lenticular (lentil-shaped) or has a non-spherical, often polyhedron-type shape and can be characterized by a non-spherical vesicle shape. The lenticular shape of the liposomes leads to surface areas with different curvatures associated with disorder/defects. At high curvatures and less ordered areas, i.e. along the equator, this generates potential breaking points. The lenticular morphology is regarded as a metastable state of minimized energy between a spherical-shaped vesicle and a flat surface. Kinetic factors such as the cooling rate and the choice of the vesicle preparation method influence the formation of faceted forms.

The term interdigitated in the context of the present specification relates to a lipid bilayer in which the acyl chains in each lipid monolayer cross the lipid bilayer midline and penetrate into the opposing monolayer, where they interact with the acyl chains of the opposing lipid monolayer. A full interdigitation describes lipid bilayers in which each acyl chain in the bilayer spans the entire width of the bilayer, i.e., where there are four acyl chains per headgroup surface area.

DETAILED DESCRIPTION OF THE INVENTION

A first aspect of the invention relates to a liposome vesicle comprising, or essentially consisting of, a membrane and a volume of an aqueous solution limited by said membrane. The membrane essentially consists of 1,3-diheptadecanamidopropan-2-yl (2-(trimethylammonio) ethyl) phosphate (4).

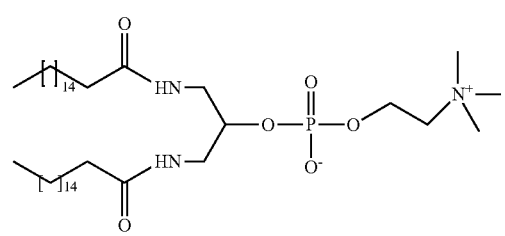

(4)

In certain embodiments, the membrane is characterized by a bilayer structure.

The liposome vesicle has a faceted form.

In certain embodiments, the bilayer structure comprises an interdigitated phase, wherein said interdigitated phase is formed within a temperature range of 41° C. to 46° C., particularly within a range of 42° C. to 46° C., more particularly within a range of 43° C. to 45.0° C., more particularly within a range of 43.7° C. to 44.7° C. or approx. at 43.7° C. or approx. at 44.7° C.

In certain embodiments, the vesicle comprises a pharmaceutical drug.

In certain embodiments, the pharmaceutical drug or active agent is selected from any one of:
- a fibrinolytic agent,
- a thrombolytic agent,
- an anti-coagulation agent,
- an anti-aggregation agent,
- an anti-thrombotic agent;
- an atherosclerotic plaque stabilizer, particularly a statin, or other related or non-related plaque stabilizers,
- a liver X receptor agonist,
- a vasodilatory agent, particularly a vasodilatory agent selected from a direct or indirect acting vasodilator, more particularly a vasodilatory agent selected from a nitric oxide liberating agent, an alpha-adrenoceptor antagonist, an angiotensin converting enzyme (ACE) inhibitor, an angiotensin receptor blocker (ARB), a direct renin inhibitor, a calcium-channel blocker (CCB), an endothelin receptor antagonist, a phosphodiesterase inhibitor, a potassium-channel opener, an anti-arrhythmic drug, particularly an anti-arrhythmic drug selected from a sodium-channel blocker, a beta-blocker, a potassium-channel blocker, a calcium-channel blocker, an inotrope positive medication, particularly pharmaceutical drug selected from a catecholamine or a non-catecholamine, heart muscle remodeling, particularly pharmaceutical drug selected from an ACE inhibitor or an ARB, diastolic dysfunction treatment, particularly a pharmaceutical drug selected from a beta blocker, an ACE inhibitor or an ARB, decongestion, particularly a pharmaceutical drug selected from a brain natriuretic peptide or nitro-release drugs, radio contrast marker, particularly a radio contrast marker for use in a computed tomography, a magnetic resonance imaging, a positron emission tomography, scintigraphy, percutaneous coronary intervention, a chemotherapeutic agent, a coagulation factor agent, an anti-inflammatory agent.

In certain embodiments, the pharmaceutical drug is selected from alteplasum, heparin, acetyl salicylic acid, clopidogrelum, glycoprotein IIb/IIIa inhibitor, rosuvastatinum, nitric oxide liberating agent, nitroprussiate, molsidomine, phentolamine, enalapril, candesartan, diltiazem, bosentan, milrinone, levosimendan, minoxidilum, aliskirenum, quinidine, metoprolol, amiodarone, verapamil, epinephrine, norepinephrine, dopamine, dobutamine, isoprenalin, levosimendan, vasopressin, glypressin, brain natriuretic peptide, nesiritidum, nitroglycerine, alteplasum, eptacogum alfa, recombinant Factor VII (NovoSeven), perlinganit, In certain embodiments, the vesicle of the invention comprises Iodine or an iodine containing contrast agent, and a gadolinium containing contrast agent.

In certain embodiments, the liposome vesicle comprises a cardiomyocyte or a stem cell. Another aspect of the invention relates to a method of preparing a vesicle comprising the steps of i. providing 1,3-diheptadecanamidopropan-2-yl (2-(trimethylammonio) ethyl) phosphate dissolved in an organic solvent, particularly a volatile organic solgent, more particularly methanol or ethanol or ethanolacetate, or dichloromethane or chloroform;

ii. removing said organic solvent under an inert atmosphere (under vacuum or under nitrogen flow), thereby obtaining a lipid sheet;

iii. suspending said lipid sheet in a first aqueous buffer solution having a physiological pH (particularly comprising 10 mmol/L HEPES), wherein said first buffer solution
comprises a chloride salt, particularly NaCl at a concentration range from about 5 mmol/L to about 15 mmol/L, particularly about 10 mmol/L; and/or
has an osmolarity in a range of 200 mOsm/L to 400 mOsm/L, particularly in a range of 280 mOsm/L to 320 mOsm/L, more particularly an osmolarity of 308 mOsm/L;

iv. applying at least one freezing step and one thawing step,
particularly wherein said freezing step is effected by a cryogenic agent such as liquid nitrogen, and wherein said thawing step is effected by rapidly bringing the sample to a temperature range of 55° C. to 70° C., particularly at 65° C., resulting in a suspension (vesicle fragmentation);

v. in an extrusion step, extruding said suspension, particularly by filtration through a filter having a pore diameter in a range of 50 nm to 150 nm, more particularly in a range of 80 nm to 120 nm, even more particularly a pore diameter of 100 nm, optionally repeating the extrusion step, particularly 5 to 15 times, thereby obtaining an extrudate;

vi. dialyzing said extrudate in a second buffer solution having a physiological pH and osmolality, to remove small molecular weight components.

In certain embodiments, the second (dialyzing) buffer comprises a chloride salt, particularly NaCl at a concentration range from about 80 mol/L to 120 mmol/L, particularly at 107 mmol/L. In certain embodiments, the buffer is buffered by ca. 10 mmol/L HEPES. Other physiological and pharmaceutically acceptable buffer systems are known in the art.

The dialysis is selected to remove molecules having a molecular weight of ≤1500 Da. Exemplary means include, but are not limited to, a Sephadex G-50 column, Illustra Sephacryl S-1000 Superfine, or a PD-10 desalting column (GE Healthcare, UK).

The vesicles of the invention can be obtained according to techniques known in the art (e.g. "Preparation of Vesicles (Liposomes)" by Peter Walde in Encyclopedia of Nanoscience and Nanotechnology, Volume 9, pp. 43-79(37)). In certain embodiments, the vesicles are produced by thin film hydration, and/or one or more freeze-thaw cycles, sonication or/and extrusion, or by an electroformation method or by hydrating spray-dried lipids or by sonication or by repetitive freezing and thawing or by dehydration and rehydration or by the extrusion technique or by the treatment of a multilamellar vesicle suspension with a microfluidizer, or the preparation of multilamellar novasomes or the preparation of multilamellar spherulites, or the preparation of multilamellar vesicles by the "bubble method" (Talsma et al., J. Pharm. Sci. 83, 276 (1994)), or the preparation by the "Cochleate cylinder method" (Gould-Fogcrite and Mannino, Liposome Technology, Vol. I, 2nd ed., edited by G. Gregoriadis, CRC Press, Boca Raton (1993), p. 67), or the preparation by the "Reversed-phase evaporation technique, or the preparation from water/oil and water/oil/water emulsions, or the preparation by the "solvent-spherule (w/o/w—emulsion) method" (Kim et al. Biochim. Biophys. Acta 812. 793 (1985)) or the "DepoFoam Technology" (Mantripragada, Progr. Lipid Res. 41, 392 (2002)), or the preparation from an organic aqueous two-phase system, or the preparation by the "ethanol injection method" (Domazou and Luisi, 1. Liposome Res. 12, 205 (2002)), or the preparation by the "pro-liposome method" (Williams et al., Phospholipids/Characterization, Metabolism, and Novel Biological Application, edited by Cevc and Paltauf, AOCS Press, Champaign IL (1995). p. 181), or the preparation of multilamellar ethosomes, or the preparation by the "interdigitation-fusion method" (Chen et al. Biochim. Biophys. Acta 1195, 237 (1994)), or the preparation by the "coacervation technique" (Ishii et al., Langmuir 11, 483 (1995)), or the preparation by the "supercritical liposome method" (Frederiksen et al., J. Pharm. Sci. 86, 921 (1997)), or the preparation from an initial oil/water emulsion, or the preparation by the "ether injection method" (Deamer, Ann. N. Y. Acad. Sci. 308, 250 (1978)), or the preparation by the "rapid solvent exchange method" (Buboltz and Feigenson, Biochim. Biophys. Acta 1417, 232 (1999)). or the preparation by the "Detergent-depletion method" (Parente and Lentz, Biochemistry 23, 2353 (1984); Allen et al., Biochim. Biophys. Acta 601, 328 (1980)), or the preparation by mixing bilayer-forming and micelle-forming amphiphiles, or the preparation from lipids in chaotropic ion solutions, or the preparation of vesicles prepared from a water/oil-emulsion with the help of a detergent.

Another aspect of the invention relates to a vesicle obtained by a process outlined above. Yet another aspect of the invention relates to the use of a compound as recited above in the treatment of
a vascular disease, or
a dermatological disease, or
an arthropathy, characterized in that the compound is administered in the form of a vesicle of the invention.

In certain embodiments, the disease treated by the compound according to the invention is a vascular disease selected from acute coronary syndrome (ACS), myocardial infarction, acute heart insufficiency, chronic heart insufficiency, cerebrovascular accident (CVA), stroke, atherosclerosis, vasospasm, tumor treatment, hemoptysis, pulmonary embolism, pulmonary arterial hypertension, intestinal ischemia, intestinal hemorrhage, renal infarction, renal hemorrhage, renal auto-regulation for hypertensive treatment, auto-immune glomerulonephritis, interstitial nephritis, fetal diseases, placental infarction, placental hemorrhage, retinal ischemia, retinal hemorrhage and retinal neovascularization.

In certain embodiments, the disease treated by the compound according to the invention is a dermatological disease and is selected from acne, napkin dermatitis, atopic dermatitis, seborrheic dermatitis, psoriasis, warts, tinea pedis, seborrheic keratosis, hives, rosacea, dermatological viral infection and dermatological bacterial infection.

Another aspect of the invention relates to the use of a vesicle according to any one of the preceding aspects or embodiments in a method of monitoring or diagnosis.

In another aspect, the invention relates to 1,3-diheptadecanamidopropan-2-yl (2-(trimethylammonio) ethyl) phosphate (4)

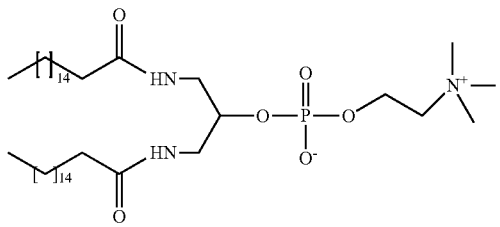

(4)

A monolayer of (4) may be obtained by dissolving (4) in an organic solvent, particularly a volatile organic solvent, for example chloroform, DCM or methanol or ethanol. The solution is added dropwise to a still surface of water or an aqueous solution, and the solvent is gently removed.

Lipid monolayers may be used for example in treatment or prevention of infant respiratory distress syndrome caused by infant surfactant deficiency.

BRIEF DESCRIPTION OF THE FIGURES

FIG. 12 2D maps of the average scattered intensity at three flow rates v in the q-range from 0.096 to 0.102 nm$^{-1}$. At the flow rate v=0:002 µL/s the intensity appears rather homogeneous on both sides of the constriction, albeit slightly higher intensity is registered on the inlet side. At higher flow rates (v=0.02; 0.2 µL/s), a signal of increased intensity with a distinct plume-like shape is visible immediately at the constriction exit, whereas at the constriction entrance the signal reveals high intensity at intermediate flow rate and reduced intensity with stagnation zones at the device walls at the highest flow rate.

FIG. 13) for the three flow rates. Especially for the highest flow rate, marked differences are seen in scattering signal, prominently at high q, indicating changes in head-to-head distance. 2D maps of average scattered intensity are shown for three selected q-ranges ($\Delta q_1$=0.04 to 0.05 nm$^{-1}$, $\Delta q_2$=0.16 to 0.17 nm$^{-1}$, and $\Delta q_3$=0.83 to 1.12 nm$^{-1}$). As in FIG. 12, the establishment of a flow field with increasing flow rate can be observed.

EXAMPLES

Figure 1:
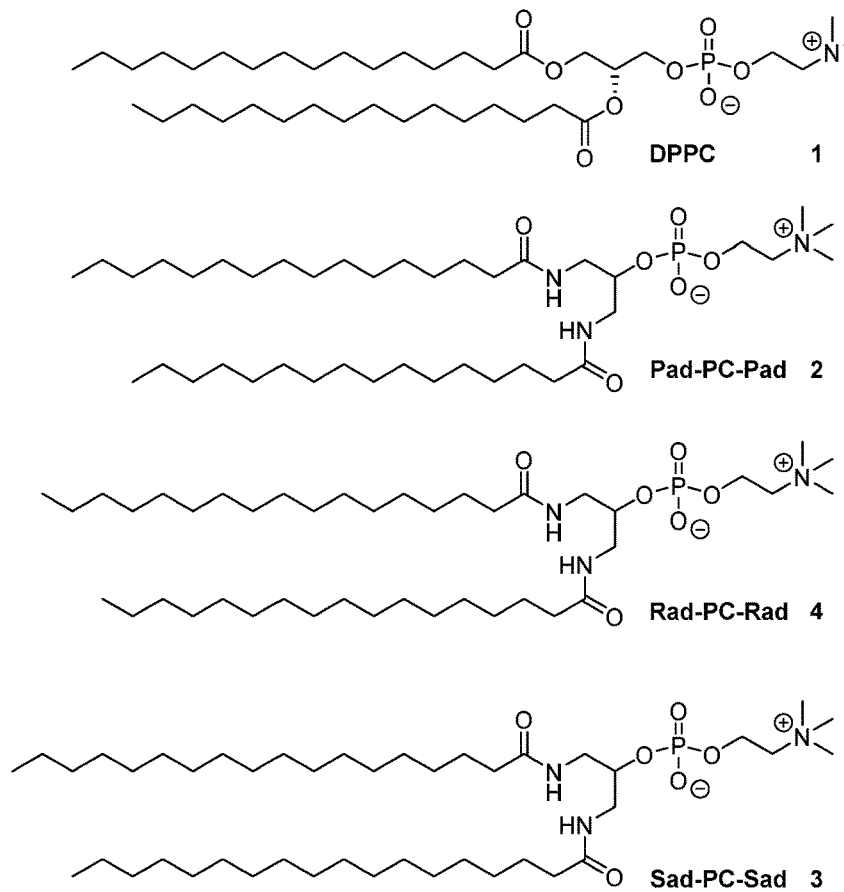
FIG. 1 shows the formulae of the natural phospholipid 1,2-dipalmitoyl-sn-glycero-3-phosphocholine and the 1,3-diamidophospholipids with C16 (1,3-palmitoylamido-1,3-deoxy-sn-glycero-2-phosphatidylcholine), C17 (1,3-diheptadecanamidopropan-2-yl (2-(trimethylammonio) ethyl) phosphate and C18 (1,3-distearamidopropan-2-phosphocholine) fatty acids.

Example 1: Synthesis of 1,3-diheptadecanamidopropan-2-yl (2-(trimethylammonio) ethyl) phosphate The 1,3-diheptadecanamidopropan-2-yl (2-(trimethylammonio) ethyl) phosphate was synthesized according to synthetic route shown in Scheme 1. A substitution of phosphorus oxytrichloride with 1,3-dichloropropanol led to a phosphorochloridate. A second substitution with Boc-protected ethanolamine led to the reasonably stable phosphoramidate (5). This intermediate was transformed into a diazide, followed by a reduction to the diamine. The heptadecanoyl chains were accessed via heptadecanoic acid chloride (6) prepared from heptadecanoic acid with thionyl chloride, and were reacted with the diamine to yield head group-protected phosphoramidate (7). The final diamidophospholipid 1,3-diheptadecanamidopropan-2-yl (2-(trimethylammonio) ethyl) phosphate (4) was reached after acidic head group deprotection and quaternization with dimethyl sulfate. The overall yield after 5 steps was 37% starting from the head group protected dichloropropyl phosphoramidate (5). The chemically pure diamidophospholipid 1,3-diheptadecanamidopropan-2-yl (2-(trimethylammonio) ethyl) phosphate was then characterized on a molecular level, as monolayers at the air-water interface (2D model) and as bulk systems (3D model).

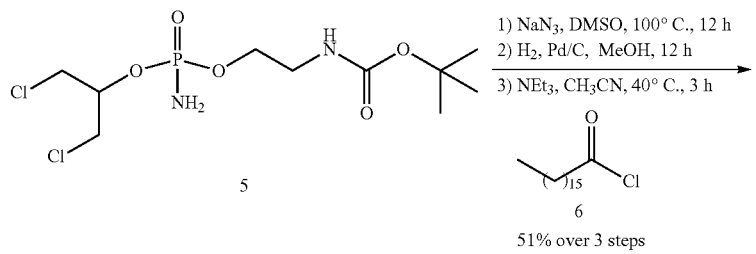

51% over 3 steps

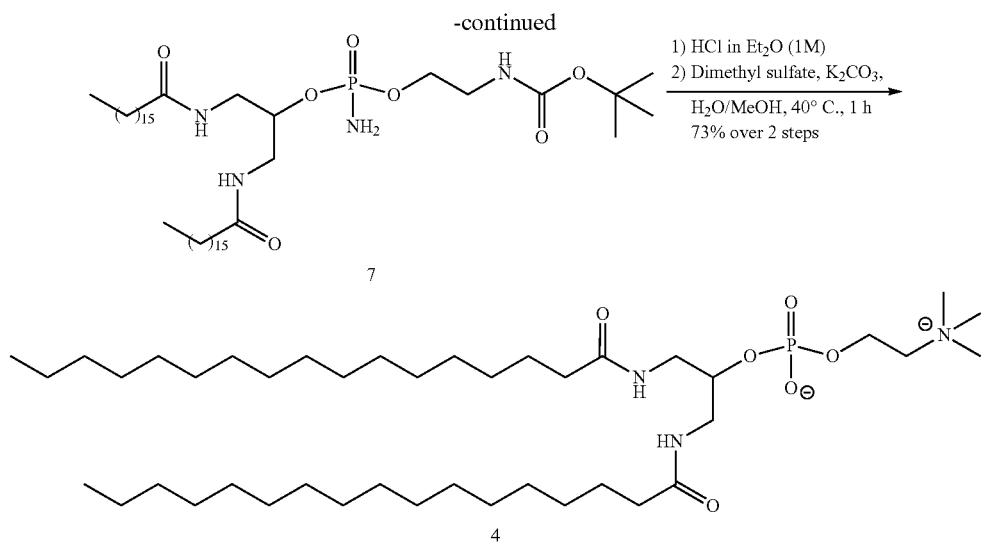

Example 2: Surface Pressure/Area Per Molecule Isotherms

Figure 2:
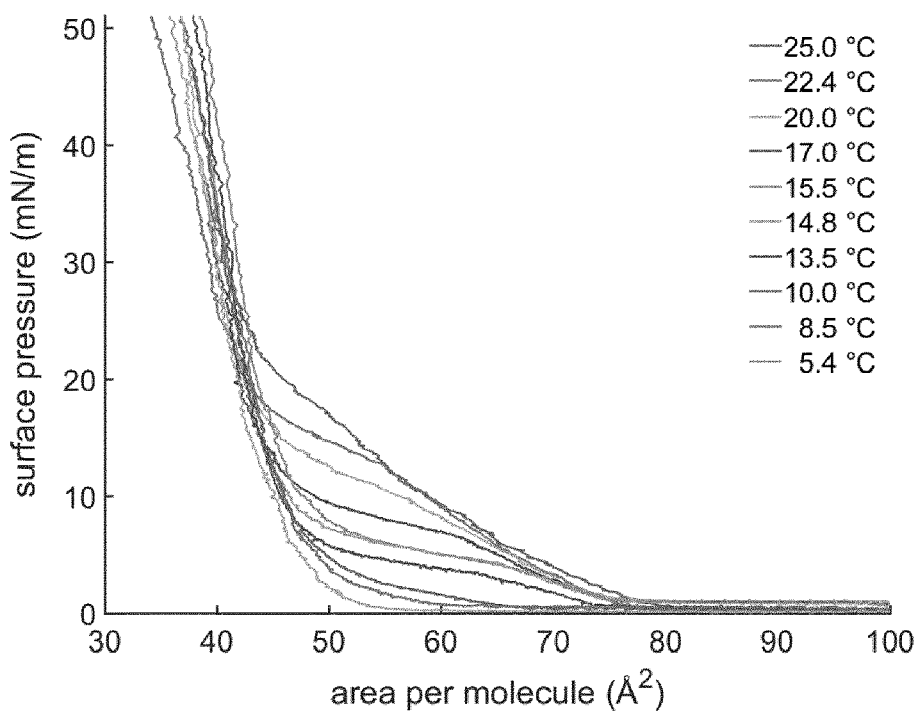
FIG. 2 shows the surface-pressure/area per molecule isotherms of a monolayer comprising 1,3-diheptadecanamidopropan-2-yl (2-(trimethylammonio) ethyl) phosphate at the air-water interface on a Langmuir-Pockels trough with an aqueous subphase at different temperatures. The surface pressure was recorded via a Wilhelmy paper balance (accuracy 0.2 mN/m).

The surface pressure/area per molecule isotherm measurements were carried out on a Langmuir-Pockels trough, equipped with a Wilhelmy paper balance (accuracy 0.2 mN/m), at the air-water interface. The isotherms were measured at different subphase temperatures between 5° C. and 25° C. (FIG. 2).

Figure 3:
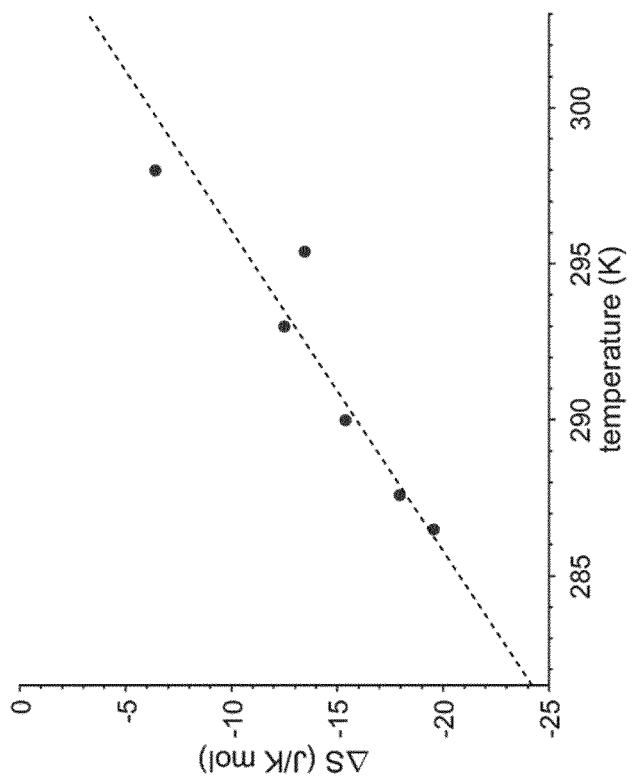
FIG. 3 shows the temperature dependence of the main phase transition pressure $\Pi_t$ (left) and temperature dependence of the entropy change ($\Delta S$) (right) at the main phase transition of monolayers comprising 1,3-diheptadecanamidopropan-2-yl (2-(trimethylammonio) ethyl) phosphate spread at the air-water interface.
Figure 3:
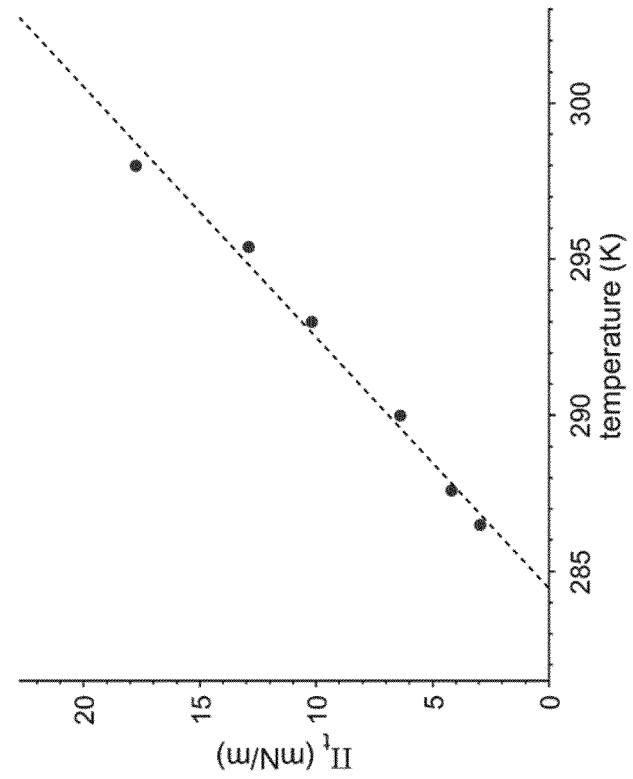

Monolayers comprising 1,3-diheptadecanamidopropan-2-yl (2-(trimethylammonio) ethyl) phosphate showed a liquid-expanded to liquid-condensed phase behavior. Above 10 C, a plateau of a mixed expanded/condensed phase transition was observed. The appearance of the plateau is accompanied by a shift of the initial lift-off area per molecule to higher values. The plateau represents the first-order phase transition from a liquid-expanded (LE) to a liquid-condensed (LC) phase. The plateau is not fully horizontal, especially it becomes steeper as the temperature increases. The monolayers themselves are stable over the measurable range of surface pressures up to an instrument-based cut-off at 51 mN/m. From the onset of the plateau it is possible to determine the temperature-dependent main transition pressure $\Pi_t$. For 1,3-diheptadecanamidopropan-2-yl (2-(trimethylammonio) ethyl) phosphate this dependence can be described by a linear function (FIG. 3). The experimental data only deviates from this linear function in close vicinity of the minimum transition temperature $T_0$ below which the transition into a condensed phase directly starts from the gas-analog state (re-sublimation process). For 1,3-diheptadecanamidopropan-2-yl (2-(trimethylammonio) ethyl) phosphate this temperature is 284.4 K.

From the area per molecule at the onset of the first-order phase transition ($A_0$) at $\Pi_t$ and the area at the end of the expanded-condensed phase coexistence (As) it is possible to calculate the enthalpy change ($\Delta H$) of the phase transition using a modified two-dimensional Clausius-Clapeyron equation.

$$\Delta H = (A_c - A_0) T \frac{d\Pi_t}{dT}$$

With this the entropy change dependency is represented by $\Delta S = \Delta H/T$, which is shown in FIG. 3. The extrapolation of $\Delta S$ to zero gives the critical temperature of monolayers comprising 1,3-diheptadecanamidopropan-2-yl (2-(trimethylammonio) ethyl) phosphate of 306.3 K. Above this temperature; no compression of the monolayer to a condensed state is possible.

Example 3: Grazing Incidence-Angle X-Ray Diffraction (GIXD)

Figure 4:
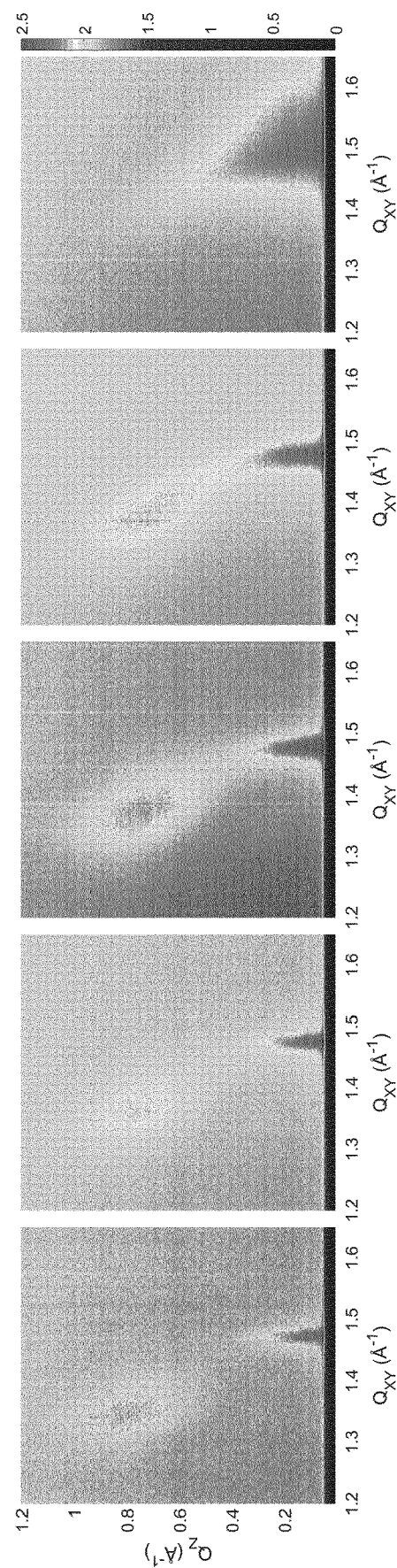
FIG. 4 shows the GIXD heatmaps of the diffraction intensities as a function of the in-plane $Q_{xy}$ and out-of-plane $Q_z$ components of the scattering vector Q for the 1,3-diheptadecanamidopropan-2-yl (2-(trimethylammonio) ethyl) phosphate (4) at 20° C. and different surface pressures π (from left to right: 14 mN/m, 18 mN/m, 22 mN/m, 26 mN/m, 36 mN/m).

GIXD experiments provide insights into the lattice structure of condensed monolayers on the angstrom scale. The in-plane component of the scattering vector ($Q_{XY}$) and out-of-plane component ($Q_Z$) maxima of the different measurements are presented in table 1 and exemplary heatmaps are shown in FIG. 4. For the 1,3-diheptadecanamidopropan-2-yl (2-(trimethylammonio) ethyl) phosphate two Bragg Peaks have been observed for every measured temperature/surface pressure combination. The signal at higher $Q_Z$ is a degenerated signal composed of two equal signals. The 1,3-diheptadecanamidopropan-2-yl (2-(trimethylammonio) ethyl) phosphate (4) monolayers adopt an orthorhombic lattice structure described by a distorted rectangular unit cell, with a distortion in the NN (nearest neighbor) direction and a fairly high tilt angle t (between 27° and 38°) of the lipid-tails tilted to the same NN direction. At 20° C., the chain cross-sectional area ($A_0$) is around 19.3 Å$^2$, and therefore only marginally larger than that observed at lower temperatures (19.0 Å$^2$ at 10° C. and 19.1 Å$^2$ at 15° C.). This is a typical value for chains in a herringbone packing mode. This packing mode is supported by the distortion value obtained by extrapolation of the distortion vs. $\sin^2(t)$. The value $d_0$ amounts to −0.0775 and is clearly different from zero which would be expected if the tilt is the only source for the lattice distortion. In the present case, the herringbone packing is an additional source and might be caused by a hydrogen-bonding network between the head groups.

Figure 5:
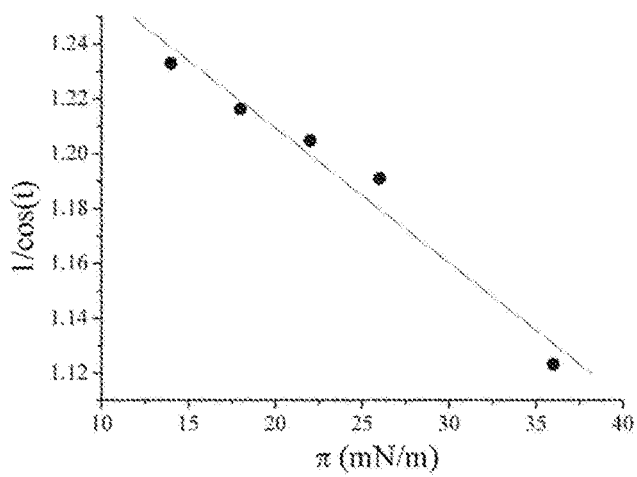
FIG. 5 shows the dependence of the tilt angle of the alkyl chains (t) represented as 1/cos(t) on the lateral surface pressure (π) at 20° C.

With increasing surface pressure the tilt angle t decreases with 0.41° per mN/m (FIG. 5). Assuming a constant cross-sectional area in the condensed phase, the tilting phase transition pressure can be determined from a plot of 1/cos(t) vs. the lateral pressure. Extrapolation to 1/cos(t)=1 yields a tilting pressure of 62.3 mN/m (FIG. 5). Such a phase transition would usually be characterized by a kink in the surface-pressure area isotherm as expected for a second-order phase transition. However, the expected transition surface pressure is too high to be observed with the used set-up. The tilting phase transition pressure can be compared to those of other lipids, like the C18-analogeous diamidophospholipid 1,3-distearamidopropan-2-phosphocholine (3). A trend is visible, with longer fatty acyl chains leading to higher tilting phase transition pressures. At 30° C., the cross-sectional area of the 1,3-diheptadecanamidopropan-2-yl (2-(trimethylammonio) ethyl) phosphate (4) of 20.2 Å² is in the expected range for rotator phases (Table 1 and FIG. 3).

Example 5: Differential Scanning Calorimetry

Interdigitation of membrane leaflets also influences the membranes main-phase transition temperature. Differential scanning calorimetry experiments from LUVs containing 1,3-diheptadecanamidopropan-2-yl (2-(trimethylammonio) ethyl) phosphate with heating and cooling rates of 0.5° C./min result in a main phase transition temperature of 44.7° C. with a change in enthalpy of 24.16 kJ/mol. The main-phase transition temperature is lower compared to a natural 1,2-diester phospholipid with margaric acid chains, which is 48.6° C. Also, the value for the bilayer main-phase transition

TABLE 1

Summarized data from grazing incidence angle X-ray diffraction measurements of monolayers comprising 1,3-diheptadecanamidopropan-2-yl (2-(trimethylammonio) ethyl)phosphate (4) at different temperatures and surface-pressures.

| T/°C. | Π | | Degen. | Non-degen. | a | b | c | α/° | β/° | γ/° | dist | τ/° | $A_{xy}$/Å² | $A_0$/Å² |
|---|---|---|---|---|---|---|---|---|---|---|---|---|---|---|
| 10 | 30 | $Q_{XY}$ | 1.34 | 1.45 | 5.57 | 5.15 | 5.15 | 114.5 | 122.8 | 122.8 | 0.108 | 38.0 | 24.1 | 19.0 |
|    |    | $Q_Z$    | 0.88 | 0.00 |      |      |      |       |       |       |       | NN   | NN   |      |
| 15 | 30 | $Q_{XY}$ | 1.36 | 1.47 | 5.51 | 5.09 | 5.09 | 114.4 | 122.8 | 122.8 | 0.109 | 35.7 | 23.6 | 19.1 |
|    |    | $Q_Z$    | 0.82 | 0.00 |      |      |      |       |       |       |       | NN   | NN   |      |
| 20 | 14 | $Q_{XY}$ | 1.34 | 1.47 | 5.61 | 5.11 | 5.11 | 113.4 | 123.3 | 123.3 | 0.127 | 35.8 | 24.0 | 19.4 |
|    |    | $Q_Z$    | 0.81 | 0.00 |      |      |      |       |       |       |       | NN   | NN   |      |
|    | 18 | $Q_{XY}$ | 1.36 | 1.47 | 5.50 | 5.08 | 5.08 | 114.4 | 122.8 | 122.8 | 0.109 | 34.7 | 23.5 | 19.3 |
|    |    | $Q_Z$    | 0.79 | 0.00 |      |      |      |       |       |       |       | NN   | NN   |      |
|    | 22 | $Q_{XY}$ | 1.37 | 1.47 | 5.47 | 5.06 | 5.06 | 114.6 | 122.7 | 122.7 | 0.105 | 33.9 | 23.3 | 19.3 |
|    |    | $Q_Z$    | 0.77 | 0.00 |      |      |      |       |       |       |       | NN   | NN   |      |
|    | 26 | $Q_{XY}$ | 1.38 | 1.47 | 5.36 | 5.04 | 5.04 | 115.7 | 122.1 | 122.1 | 0.084 | 32.9 | 22.9 | 19.2 |
|    |    | $Q_Z$    | 0.76 | 0.00 |      |      |      |       |       |       |       | NN   | NN   |      |
|    | 36 | $Q_{XY}$ | 1.43 | 1.48 | 5.13 | 4.95 | 4.95 | 117.7 | 121.1 | 121.1 | 0.046 | 27.1 | 21.7 | 19.3 |
|    |    | $Q_Z$    | 0.63 | 0.00 |      |      |      |       |       |       |       | NN   | NN   |      |
| 30 | 26 | $Q_{XY}$ | 1.37 | 1.47 | 5.46 | 5.07 | 5.07 | 114.8 | 122.6 | 122.6 | 0.101 | 29.2 | 23.3 | 20.3 |
|    |    | $Q_Z$    | 0.64 | 0.00 |      |      |      |       |       |       |       | NN   | NN   |      |
|    | 34 | $Q_{XY}$ | 1.38 | 1.47 | 5.41 | 5.05 | 5.05 | 115.2 | 122.4 | 122.4 | 0.094 | 28.8 | 23.1 | 20.2 |
|    |    | $Q_Z$    | 0.64 | 0.00 |      |      |      |       |       |       |       | NN   | NN   |      |

$A_{xy}$: in-plane area per chain;
$A_0$: cross-sectional area per chain with $A_0 = A_{xy} \cos\tau$.

Example 4: Cryo-Transmission Electron Microscopy (Cryo-TEM)

Figure 6:
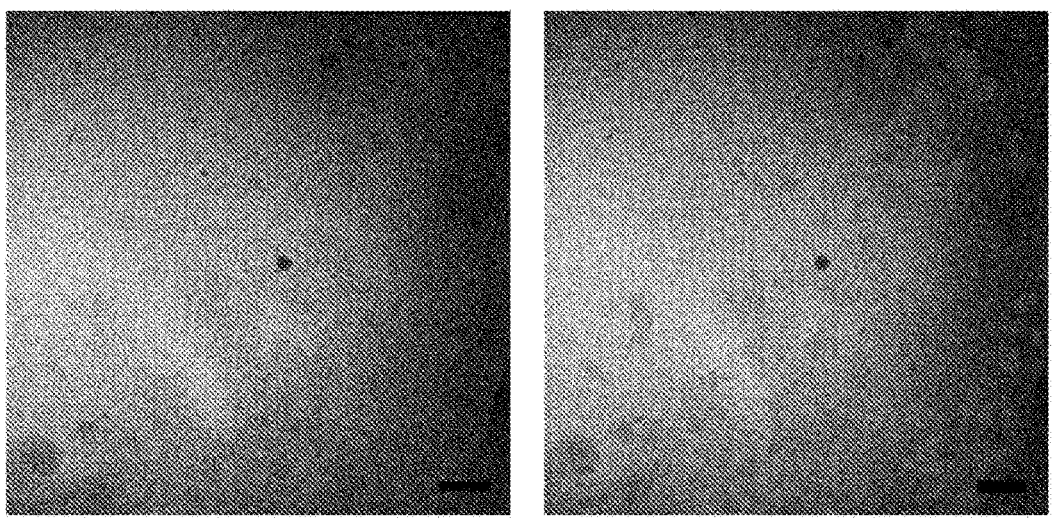
FIG. 6 shows a cryo-TEM image with highlighted measured membrane cross-sections (left, highlighted as white stripes through the membrane) and colored vesicles for statistical evaluation of the spherical to facetted ratios (orange facetted; green spherical) (scale bars are 200 nm).
Figure 7:
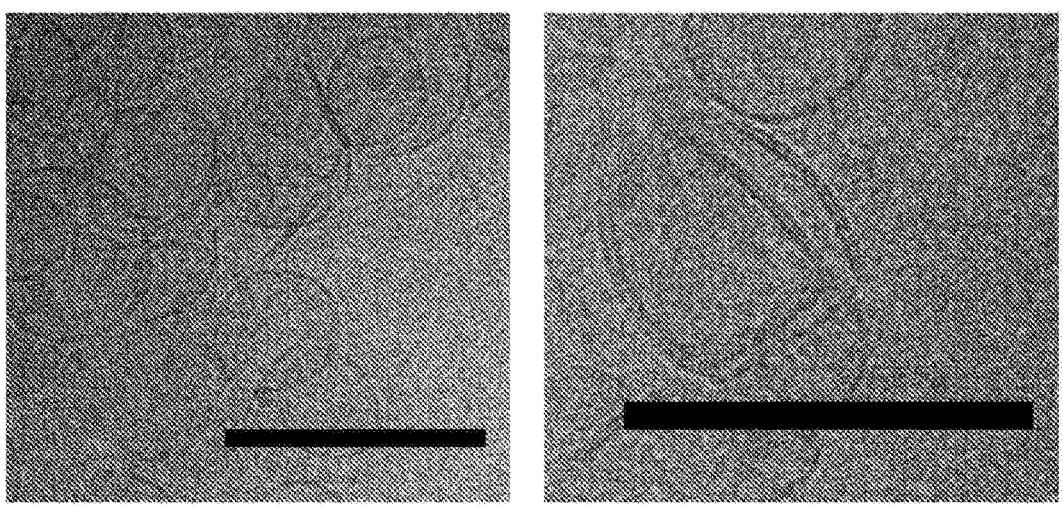
FIG. 7 shows the cryo-TEM images zoomed in to different sections of the full image to highlight vesicle structures (scale bars are 200 nm).

The inventors measured the cryo-TEM images according to a previously described protocol (Ishikawa et al, J. Mol. Biol. 2007, 368 (5), 1249-1258). The cryo-TEM images recorded from large unilamellar vesicles (LUV) entirely made of Rad-PC-Rad, show a significant number of strongly facetted shapes below the membranes' main phase transition temperature of the membranes ($T_m \approx 45°$ C.) (FIGS. 6 and 7). The ratio between facetted and spherical vesicles calculated from FIG. 6 is 21:4. The still occurring spherical shape might be due to small impurities in the prepared lipid membranes, as already small amounts of interface-active compounds can significantly influence the membrane shape and behavior.

The interdigitation of the leaflets in a membrane can be directly measured from lateral cuts through the membrane in the cryo-TEM image (FIG. 6). To collect statistically relevant data, the inventors measured 509 membrane cuts (FIG. 6) with a mean membrane thickness of 3.20 nm±0.02 nm (N=509). With two times 0.7 nm for the headgroups, the hydrophobic layer is 1.8 nm thick. An all-trans alkyl chain of 16 C-atoms has a length of 2.05 nm. Thus, the alkyl chains would have a tilt angle of 64°, which is physically absurd. Therefore, a full bilayer interdigitation can be assumed.

temperature is 11.5 K higher than the calculated critical temperature from the monolayer experiments, where no interdigitation is possible.

As the main-phase transition temperature of vesicles containing 1,3-diheptadecanamidopropan-2-yl (2-(trimethylammonio) ethyl) phosphate is well above human body temperature, these mechanosensitive liposomes are of interest for targeted drug release. To investigate the liposomes potential in this regard, release experiments were carried out.

Example 6: Release Experiments

Previously the inventors reported the 5(6)-carboxyfluorescein release from vesicles containing 1,3-palmitoylamido-1,3-deoxy-sn-glycero-2-phosphatidylcholine (2) (Holme et al., Nat. Nanotechnol. 2012, 7, 536-543). As 1,3-palmitoylamido-1,3-deoxy-sn-glycero-2-phosphatidylcholine (2) shows a strong spontaneous release already at temperatures slightly above its main-phase transition temperature ($T_m$=37° C.), the use of this lipid at the average human body temperature of 37° C. is not ideal. Increasing the $T_m$ promises improved release properties. With the longer chain-length compared to 1,3-palmitoylamido-1,3-deoxy-sn-glycero-2-phosphatidylcholine, 1,3-diheptadecanamidopropan-2-yl (2-(trimethylammonio) ethyl) phosphate has a higher main-phase transition temperature of 44.7° C. This leads to a lower leakage of the vesicles at 22°

Figure 8:
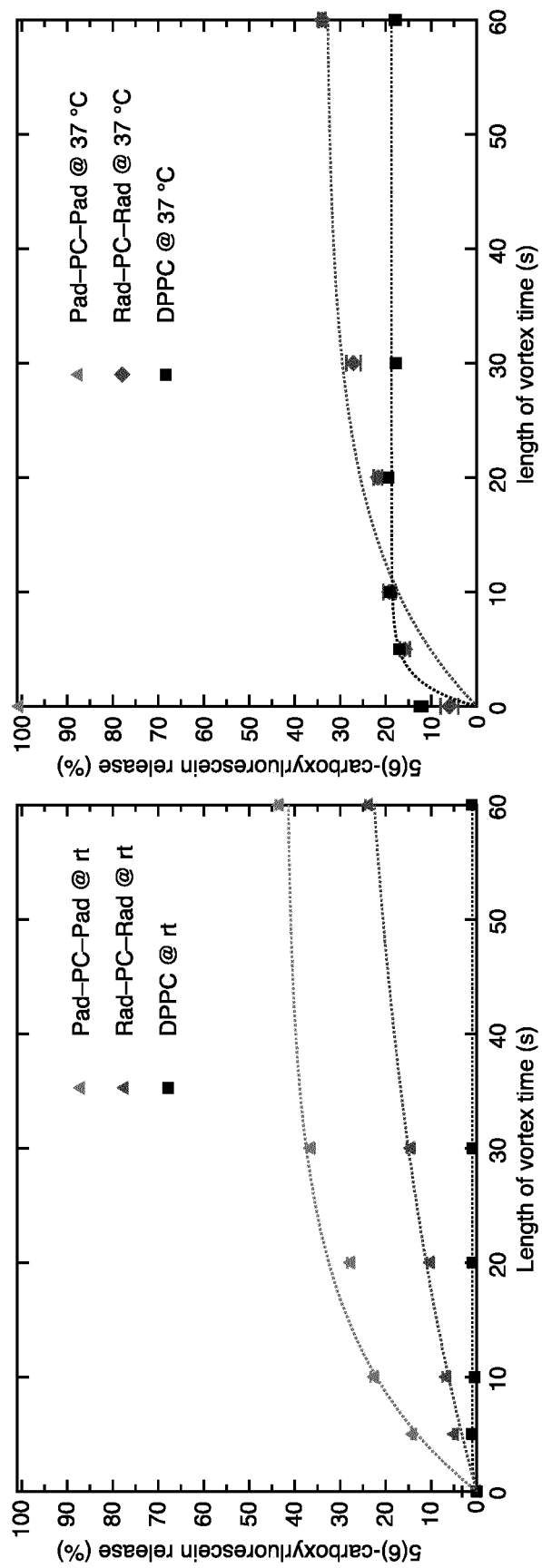
FIG. 8 Release experiments using 5(6)-carboxyfluorescein-loaded large unilamellar vesicles comprising 1,3-diheptadecanamidopropan-2-yl (2-(trimethylammonio) ethyl) phosphate (4) obtained via extrusion through a 100 nm track-edged filter membrane (LUVET$_{100}$). Triggered release was induced by shaking the samples for a specific amount of time on a vortex-shaker. The 1,3-palmitoylamido-1,3-deoxy-sn-glycero-2-phosphatidylcholine (2) at 37° C. showed an immediate full release of its cargo without shaking.
Figure 9:
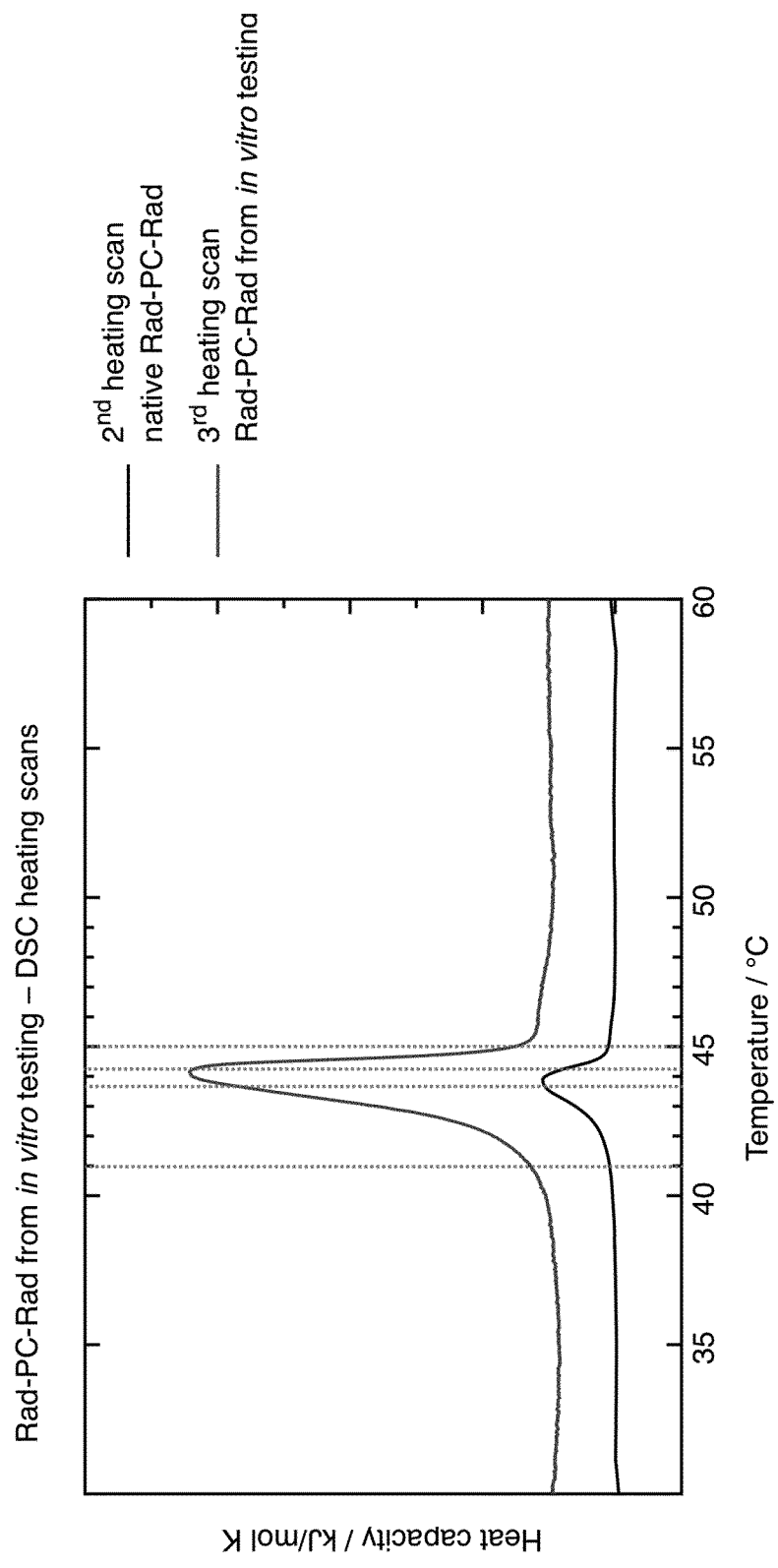
FIG. 9 shows a calorigram of (4) in aqueous NaCl. The curve represents the distribution of shapes and sizes of the generated vesicles of an exemplary sample.
Figure 10:
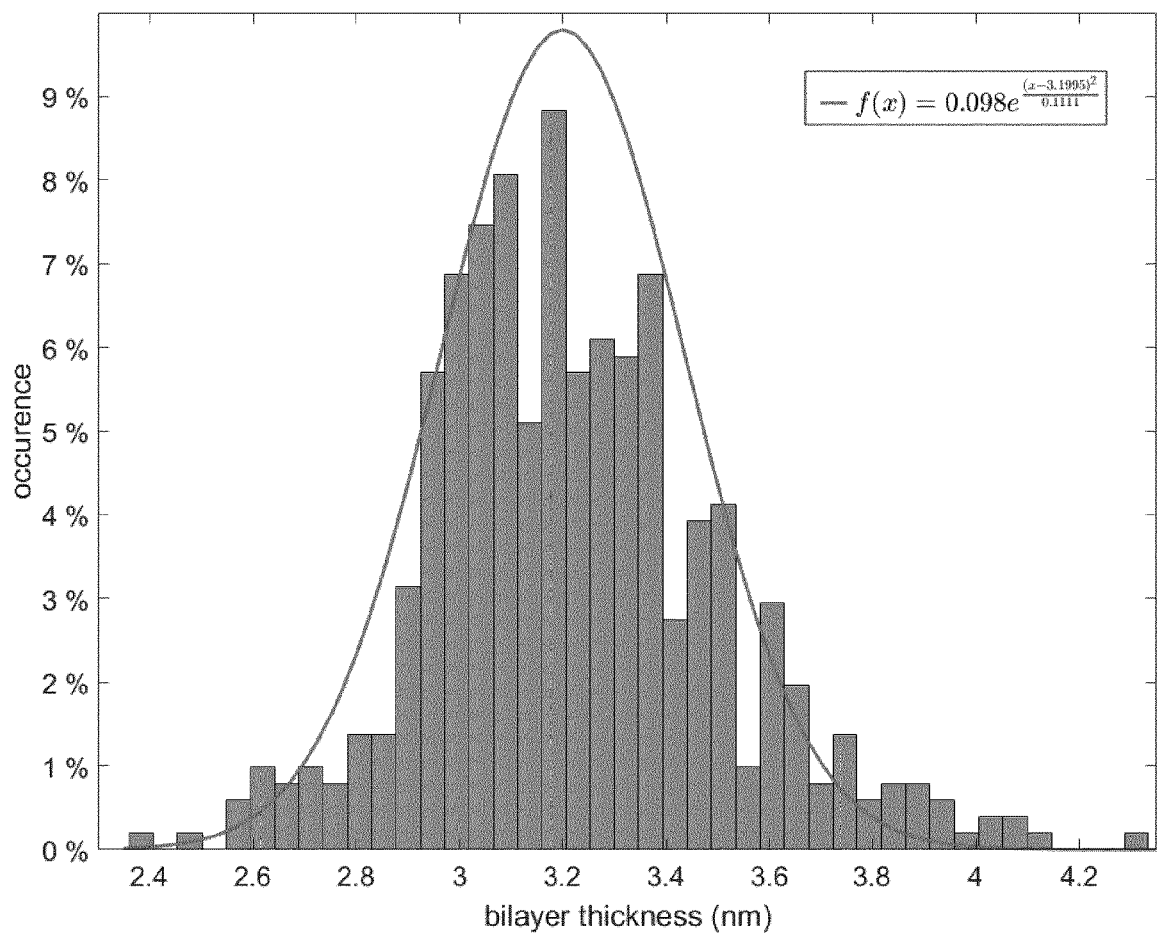
FIG. 10 shows the membrane thickness distribution of N=509 membrane cuts through Rad-PC-Rad containing vesicle membranes and a Gaussian fit.

C. (room temperature) as well as 37° C. (average human body temperature) (FIG. 8). A prolongation if the acyl chain to the artificial C18 phospholipid 1,3-stearoylamido-1,3-deoxy-sn-glycero-2-phosphatidylcholine leads to an increased $T_m$ of 52° C., but this phospholipid forms almost no liposomes anymore.

Each sample was treated with Triton X-100 to induce a full release of 5(6)-carboxy fluorescein. At a temperature of 22° C., vesicles comprising 1,3-diheptadecanamidopropan-2-yl (2-(trimethylammonio) ethyl) phosphate show a spontaneous release of 9% 5(6)-carboxyfluorescein after 7 days with a mechanically induced release of 24% after 60 s of vortexing. The vesicles comprising 1,3-palmitoylamido-1,3-deoxy-sn-glycero-2-phosphatidylcholine has a mechanically induced release of 43.4% after 60 s of vortexing and it shows a spontaneous release of 15.5% after 7 days. The vesicles comprising 1,2-dipalmitoyl-sn-glycero-3-phosphocholine (DPPC) show a mechanically induced release of 1.1% after 60 s vortexing and a spontaneous release after 7 days of 4.5%. At 37° C. the mechanically induced release of vesicles comprising 1,3-diheptadecanamidopropan-2-yl (2-(trimethylammonio) ethyl) phosphate (Rad-PC-Rad) after 60 s of vortexing is 34%, while vesicles comprising 1,3-palmitoylamido-1,3-deoxy-sn-glycero-2-phosphatidylcholine (Pad-PC-Pad) show 100% release without vortexing and vesicles comprising 1,2-dipalmitoyl-sn-glycero-3-phosphocholine shows 17.9% release after 60 s of vortexing (Table 2).

The release experiments show the potential of vesicles containing 1,3-diheptadecanamidopropan-2-yl (2-(trimethylammonio) ethyl) phosphate for targeted mechanoresponsive drug release at body temperature.

TABLE 2

Release rates of liposomes of different phospholipids.

| Name | Tm | Release at RT after 7 days | Release at RT after 60 s vortex | Release at 37° C. after 2 h | Release 37° C. after 60 s vortex |
|---|---|---|---|---|---|
| DPPC | 41° C. | 4.5% | 1.1% | 12.2% | 17.9% |
| Pad-PC-Pad | 37° C. | 15.5% | 43.4% | 100% | 100% |
| Rad-PC-Rad | 45° C. | 9.4% | 23.8% | 6% | 34.0% |
| Sad-PC-Sad | 52° C. | 8.4% (6 days) | 8.32% | 9.1% | 40.2% |

Example 7: Vesicle Preparation

Large unilamellar vesicles with a diameter of 100 nm (LUVET$_{100}$) of the 1,3-diheptadecanamidopropan-2-yl (2-(trimethylammonio) ethyl) phosphate (4) were prepared following the extrusion protocol: in a 25 ml round bottom flask, 10 mg of the lipid was dissolved in $CH_2Cl_2$. After evaporation of the organic solvent, the film was further dried under high vacuum (40 mbar) overnight. Then the film was hydrated with the internal buffer for 30 min (1 ml, 50 mM 5(6)-carboxyfluorescein, 10 mM HEPES buffer (AppliChem), 10 mM NaCl dissolved in pure water, pH 7.4). Now at least 5 freeze-thaw cycles (liquid $N_2$ to 65° C.) were carried out before the suspension was extruded 11 times using a Mini Extruder (Avanti Polar Lipids, USA) using track-edged filters with a mesh size of 100 nm (Whatman, USA). The external buffer was then exchanged on a size exclusion column (1.5×20 cm Sephadex G-50 column) in external buffer (107 mM NaCl dissolved in ultrapure water, 10 mM HEPES, pH 7.4).

Example 8: Liposomes Characterization

The final concentration of Pad-PC-Pad liposomes was (19.6+/−1.3) mg/mL, whereas that of DPPC/DSPE-PEG was (20.2+/−6.5) mg/mL.

The DLS results showed a mean diameter of (131.6+/−0.9) nm for Pad-PC-Pad and a polydispersity index (PDI) of (0.103+/−0.009), whereas for DPPC/DSPE-PEG a mean diameter of (101.3+/−0.5) nm and PDI of (0.256+/−0.005) was found.

Example 9: SAXS Measurement Under Static Conditions

Figure 11:
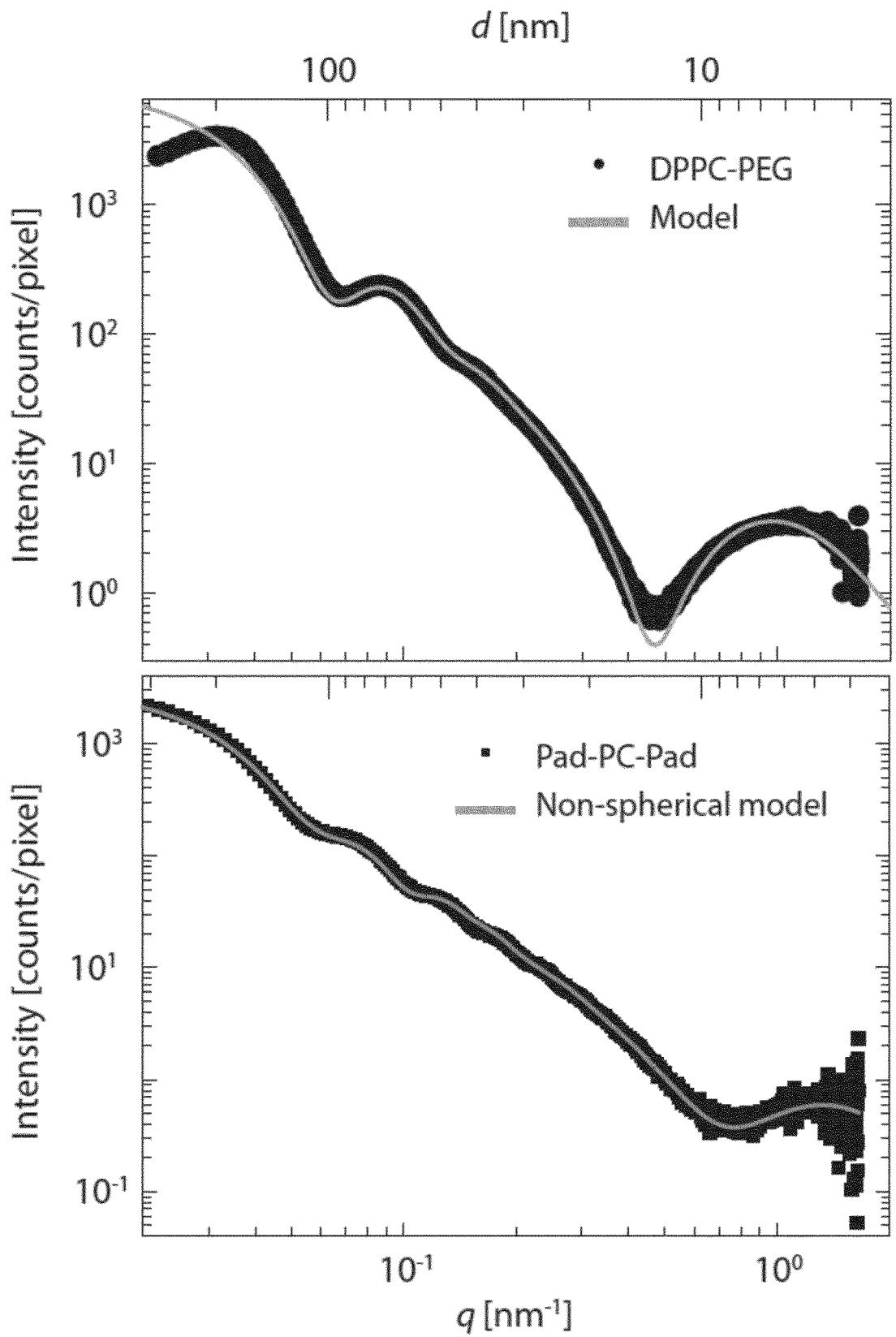
FIG. 11 Integrated scattering signals of DPPC/DSPE-PEG (black dots, top diagram) and Pad-PC-Pad (black squares, bottom diagram) under static condition. The DPPC/DSPE-PEG signal was fitted with a thin spherical shell model and a bilayer Gauss electron density profile model (grey line, top panel) with head-to-head distance $d_{hh}$=2.4 nm and 2σ=3.0 nm over the two phospholipid heads. Pad-PC-Pad scattering signal was fitted with a thin ellipsoidal shell model and a bilayer Gauss electron density profile model (grey line, bottom panel) with eccentricity ε of 0.43, head-to-head distance of $d_{hh}$=3.3 nm and 2σ=1.4 nm over the two phospholipid heads.

The investigated q-range between 0:02 $nm^{-1}$ and 1:65 $nm^{-1}$ corresponds to real-space distances d between 314 and 3 nm and, therefore, covers almost the entire nanometer range relevant for the characterization of the liposomes. The diagrams in FIG. 11 show the radially integrated scattering signal of DPPC-DSPE/PEG (top panel) and Pad-PC-Pad (bottom panel) liposomes acquired in suitable glass capillaries.

For DPPC/DSPE-PEG, the intensity peak at around 1:1 $nm^{-1}$, corresponding to 5:7 nm in real space, relates to the bilayer thickness.

For Pad-PC-Pad, the peak related to bilayer thickness is located at the edge of the detectable q-range, which additionally incurs into increased noise, and thus cannot be unequivocally characterized.

Suitable models are often utilized in the interpretation of the scattering signal of the system investigated. Herein, the scattering curves of DPPC/DSPE-PEG and Pad-PC-Pad were both fitted using a decoupling approach, which allowed to factorize the total form factor as product of a cross section term for long dimension and a cross section term for shorter dimension (Porod et al., IV. Acta Physica Austriaca 1948, 2, 255-292). To fit the form factor related to the overall shape of DPPC/DSPE-PEG, a thin spherical shell model was used (Breÿler et al., Journal of Applied Crystallography 2015, 48, 1587-1598), whereas the intensity peak related to the bilayer was fitted using a function for a bilayer with a Gaussian electron density profile (Pabst et al., Journal of Applied Crystallography 2003, 36, 1378-1388; Pabst et al., Physical Review E 2000, 62, 4000). The model utilized to fit the bilayer provided the bilayer thickness as the distance head-to-head $d_{hh}$ between the two phospholipid heads and the standard deviation over the phoshpolipid heads.

To account for the polydispersity, the radii R and the $d_{hh}$ were assumed to be normally distributed with means R=44.6 nm and $d_{hh}$=2.4 nm.

The DPPC/DSPE-PEG liposomes mean diameter of 89.2 nm is smaller than the mean value obtained from the DLS (101.3 nm). It has been reported that DLS provides values up to 20% higher compared to SAXS, as in SAXS solvent contrast variation does not allow to detect the hydrodynamic size of PEG bound to the liposomes surface. As displayed in FIG. 11 the drop in intensity of the scattering curve of DPPC/DSPE-PEG at the lowest q-values is attributed to inter-particle interference. The addition of PEG was reported to prevent liposomes aggregation, i.e. providing for a repulsive interaction between the particles. In the model utilized, PEG contribution was not included.

The distance head-to-head $d_{hh}$=2.4 nm found for DPPC/DSPE-PEG is in line with the bilayer thickness value of 5.6 nm reported in (Wang et al., Journal of Colloid and Interface Science 2015, 445, 84-92), if one includes the calculated standard deviations $2\sigma$=3:0 nm over the two phospholipid heads.

To fit the form factor related to the overall shape of Pad-PC-Pad a thin ellipsoidal shell model was used (Olson et al., Biochimica et Biophysica Acta (BBA)—Biomembranes 1979, 557, 9-23). An eccentricity E of 0.43 was found. As for DPPC/DSPE-PEG, the intensity peak related to the phospholipid head-to-head distance $d_{hh}$ was fitted using a function for a bilayer with a Gaussian electron density profile (Pabst et al., Journal of Applied Crystallography 2003, 36, 1378-1388; Pabst et al., Physical Review E 2000, 62, 4000) and a normal distribution over $d_{hh}$. The results showed a mean value of $d_{hh}$=3.3 nm and standard deviation of $2\sigma$=1:4 nm over the two phospholipid heads.

At low q-values of Pad-PC-Pad scattering curve, the Guinier approximation (Guinier, Annales de Physique 1939, 11, 161-237) was used to determine the radius of gyration ($R_g$) and found $R_g$=60.3 nm with standard deviation $\sigma_{Rg}$=0.4 nm (see Table 4), in line with the averaged diameter value obtained from the DLS (131.6 nm).

Example 9: SAXS Measurements of Pad-PC-Pad Under Dynamic Condition

Figure 12:
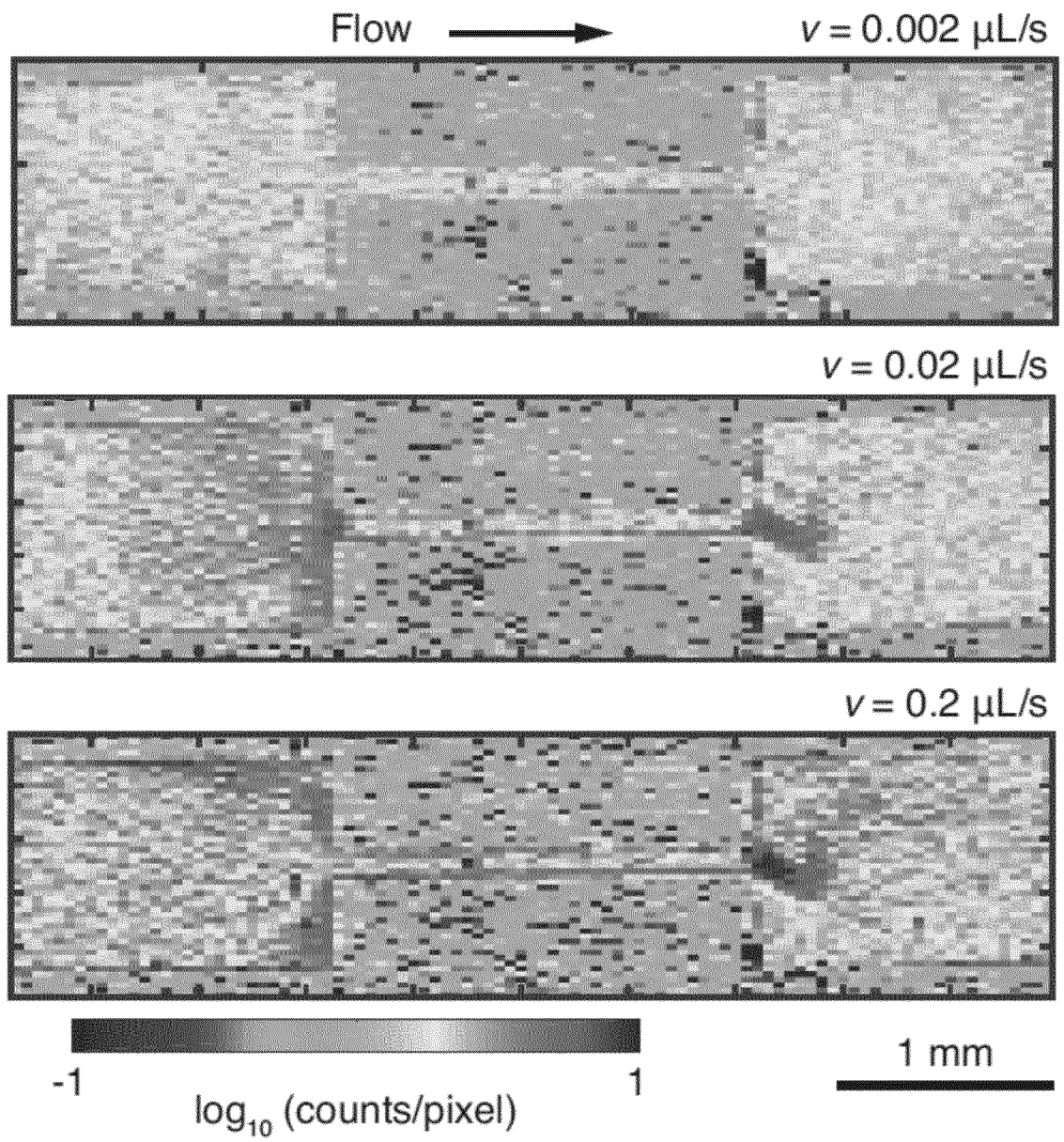

The measurement in glass capillaries provided the fingerprint of Pad-PC-Pad liposome structure in static condition. In order to investigate the behavior of Pad-PC-Pad liposomes under an external perturbation, such as a shear stress gradient, 2D raster SAXS scans of Pad-PC-Pad liposomes under flow conditions, produced in a microfluidic device, were recorded. Three flow velocities v were tested: v=0.002; 0.02; and 0.2 µL/s. The corresponding shear rates were determined using Eq. 1. From the lowest to the highest flow rate, the shear rates in the constriction (h=250 µm, w=125 µm) were=1.54, 15.4, and 154.0 s$^{-1}$, whereas in the wide region (h=250 µm, w=1000 µm) they corresponded to =0.2 s$^{-1}$, 2.0 s$^{-1}$, and 20.0 s$^{-1}$ 2 D maps of the mean scattering intensity in the range $\Delta q$=0:096 to 0:102 nm$^{-1}$ corresponding to a real space range $\Delta d$=65.4 to 61.6 nm between the overall size and the size of the phospholipid head-to-head distance are shown in FIG. 12.

The non-symmetric intensity distribution observed in the 2D maps is indicative of the complex behavior of the liposomes under varying flow conditions, and it is apparent that the flow rate, and as a consequence, the shear stress, affects the liposomes, giving rise to variations in scattering signal depending on the location within the device. At the lowest flow rate, slightly increased intensity on the inlet side was observed.

At the intermediate flow rate, the constriction significantly changed the flow field, which accelerated approaching the constriction, diverged in a plume-like shape immediately after the constriction, and finally decelerated far from the constriction. Surprisingly, within the constriction and for the whole length of it, the scattering signal decreased with respect to its entrance.

For the highest flow rate, a similar behavior was observed, with the difference that the intensity distribution at the inlet was "inverted", i.e. stronger along the device walls. This stronger intensity at the device walls is indicative of a stagnation-zone, which was already incipient at the intermediate flow rate. Immediately after the constriction, a high-intensity "plume" akin to that at the intermediate flow rate was observed.

Figure 13:
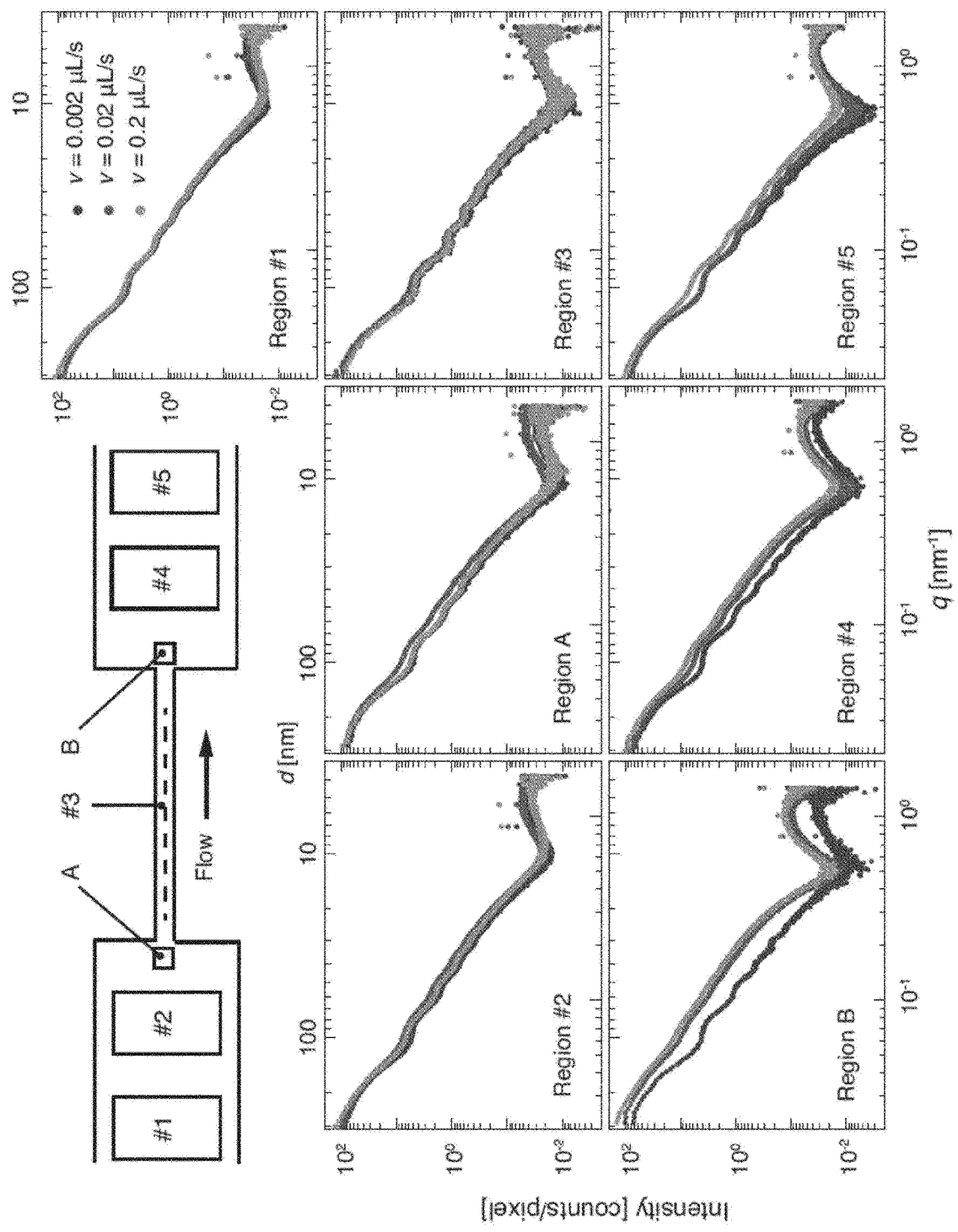
FIG. 13 Top left, sketch of the microfluidic device showing the seven regions selected. For each region, the radially integrated scattering signal is plotted for the three flow rates (v=0.002 μL/s in blue, v=0:02 μL/s in green, and v=0.2 μL/s in orange). Differences at high q-values are apparent in the regions before and after constriction, indicating changes in bilayer thickness, and are pronounced at higher flow rates.

The local modifications of the averaged scattering intensity distribution observed in the 2D scanning SAXS maps of FIG. 12 supported the selection of seven regions of the micro fluidic device, as shown in the sketch of FIG. 13. Three regions were selected before the constriction: one far (#1), one approaching (#2), and one very close (A); symmetrically, on the outlet side, three areas were chosen one very close (B), one close (#4), and one far from the constriction (#5). Region #3 was selected in the constriction avoiding the edges of the device. For each region, the radially integrated scattering intensity I as a function of the scattering vector q at each flow rate v is shown.

On the inlet side (regions #1 and #2) no significant change at low and medium q can be observed as a function of v.

The oscillations of I(q) observed at medium q overlap, indicating similar shape and size distributions of the liposomes. In contrast, the head-to-head distance $d_{hh}$ slightly decreased with increasing flow, indicated by the shift of the position of the minimum to higher q (see Table 3).

In region A at the lowest flow rate, the scattering signal was comparable to the one observed in regions #1 and #2 at all q-ranges. At the intermediate flow rate and at intermediate q the oscillations smeared out. The smearing might indicate a change in the overall shape of the liposomes.

At v=0:2 µL/s, the oscillation appeared again more pronounced, similar to the lowest flow rate, and the position of the minimum shifted to the right, in line with a decrease of $d_{hh}$. Within the constriction (region #3), the scattering curves of the liposomes did not display any significant difference by varying the flow rate. However, an increase of the $R_g$ values was observed at the three flow rates (see Table 4) with respect to the static condition and the regions before the constriction. No significant change in the $d_{hh}$ values was detected. It should, however, be noted that the signal from the constriction is less reliable due to residual edge scattering from the device walls.

At the constriction exit (region B) the oscillations, still pronounced at the lowest flow rate, smeared out completely at the intermediate and high flow rate. In fact, the $R_g$ values reported in Table 4 were comparable to the value found under static condition, but showed a decrease of about 13% at higher flow rate. Furthermore, the minimum shifted to lower q values, from 0.50 to 0:45 nm$^{-1}$ indicating that in this region, the flow field caused an increase of $d_{hh}$ of about 30% compared to the static condition (see Table 3).

The increase of the bilayer thickness of Pad-PC-Pad is in line with a mechanically induced loss of full interdigitation of phospholipid amide chains, which is usually observed at the liquid-crystalline phase (above the transition temperature) and, in presence of cholesterol, at the gel phase (below the transition temperature). In region #4, the scattering signal gradually reduced. For the intermediate and high flow rates the oscillations were smeared, as in region B, whereas for the lowest flow rate the oscillations were well visible, as in region #2. The position of the minimum did not vary significantly among the three flow rates, indicating no significant modification on the bilayer thickness.

In region #5 and at the three flow rates, the oscillations appeared similar as in region #1. In contrast, the position of the minimum, at the highest flow rate, shifted slightly to the right, from 0.55 to 0:6 nm$^{-1}$, compared to the intermediate and lowest flow rate.

Due to the impact of the local flow field, alteration of the liposomes morphology in regions A and B is detected (see FIG. 13), both at the high and low q, compared to the other regions where modifications, by varying the flow rate, were observed either at low q (e.g., region #5) or at high q (e.g., region #1, #2).

Figure 14:
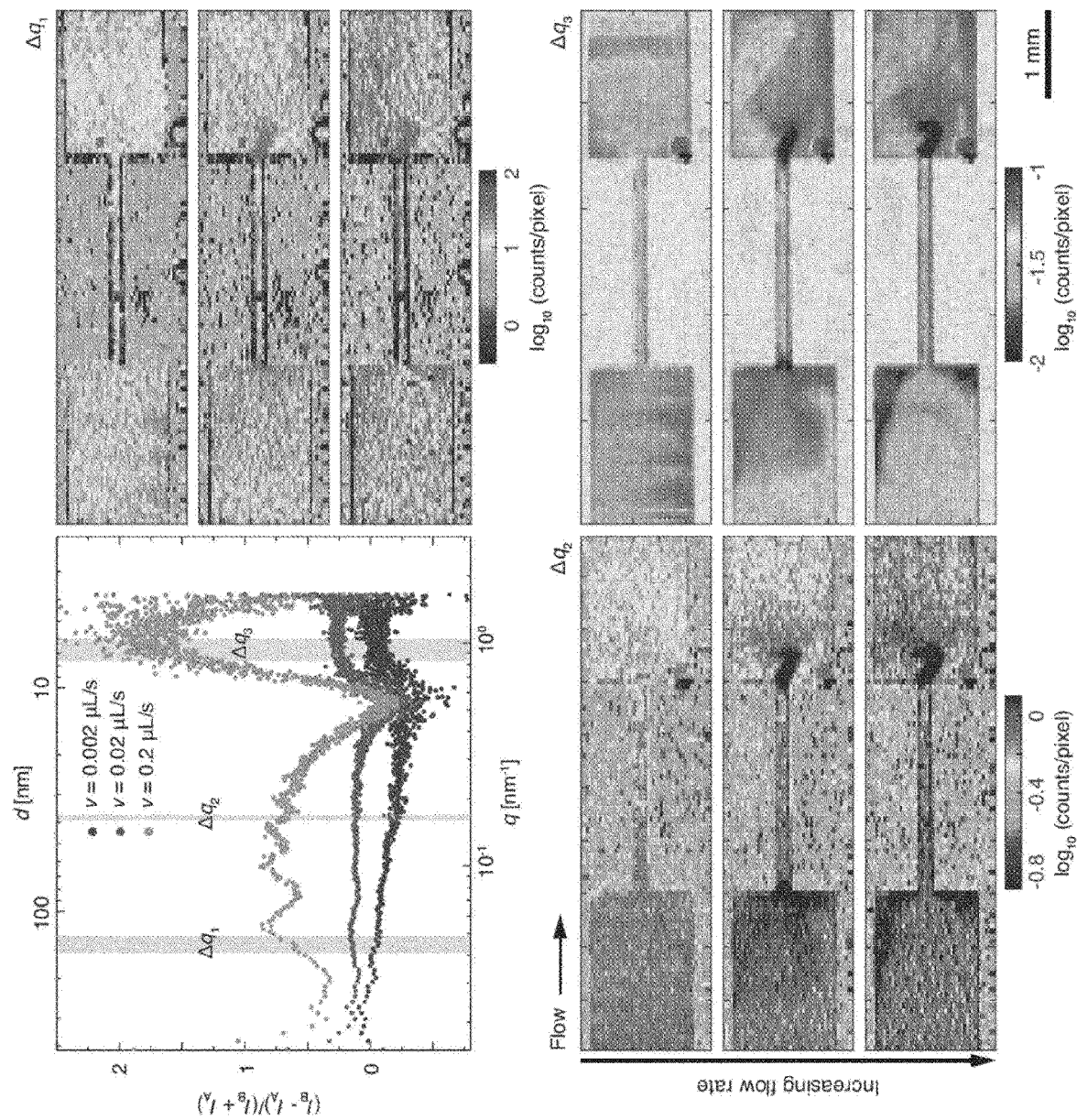
FIG. 14 The graph shows the normalized difference $(I_B-I_A)/(I_B+I_A)$ of the I vs. q curves in regions A and B (cf.

To highlight the changes of regions A (before constriction) and B (after constriction) at the three flow rates (see FIG. 13), the scattering curves in these two regions were displayed as normalized difference of their scattering intensities (see graph in FIG. 14).

Herein, three Δq ranges were selected including the mean overall size of the liposomes ($\Delta q_1$=0.04-0.05 nm$^{-1}$), the size around the bilayer thickness ($\Delta q_3$=0.83-1.12 nm$^{-1}$) and a range in between ($\Delta q_2$=0.16-0.17 nm$^{-1}$). 2D maps of the integrated scattered intensity in each selected Δq at each flow rate are displayed.

The 2D map at the lowest flow rate and in the range $\Delta q_3$ (see FIG. 14, bottom right), showed vertical stripes before and after the constriction, clear sign of the presence of artifacts within the microfluidic device. At the three Δq ranges selected, the 2D maps (see FIG. 14) a trend comparable to the one shown in FIG. 12 was observed.

Figure 15:
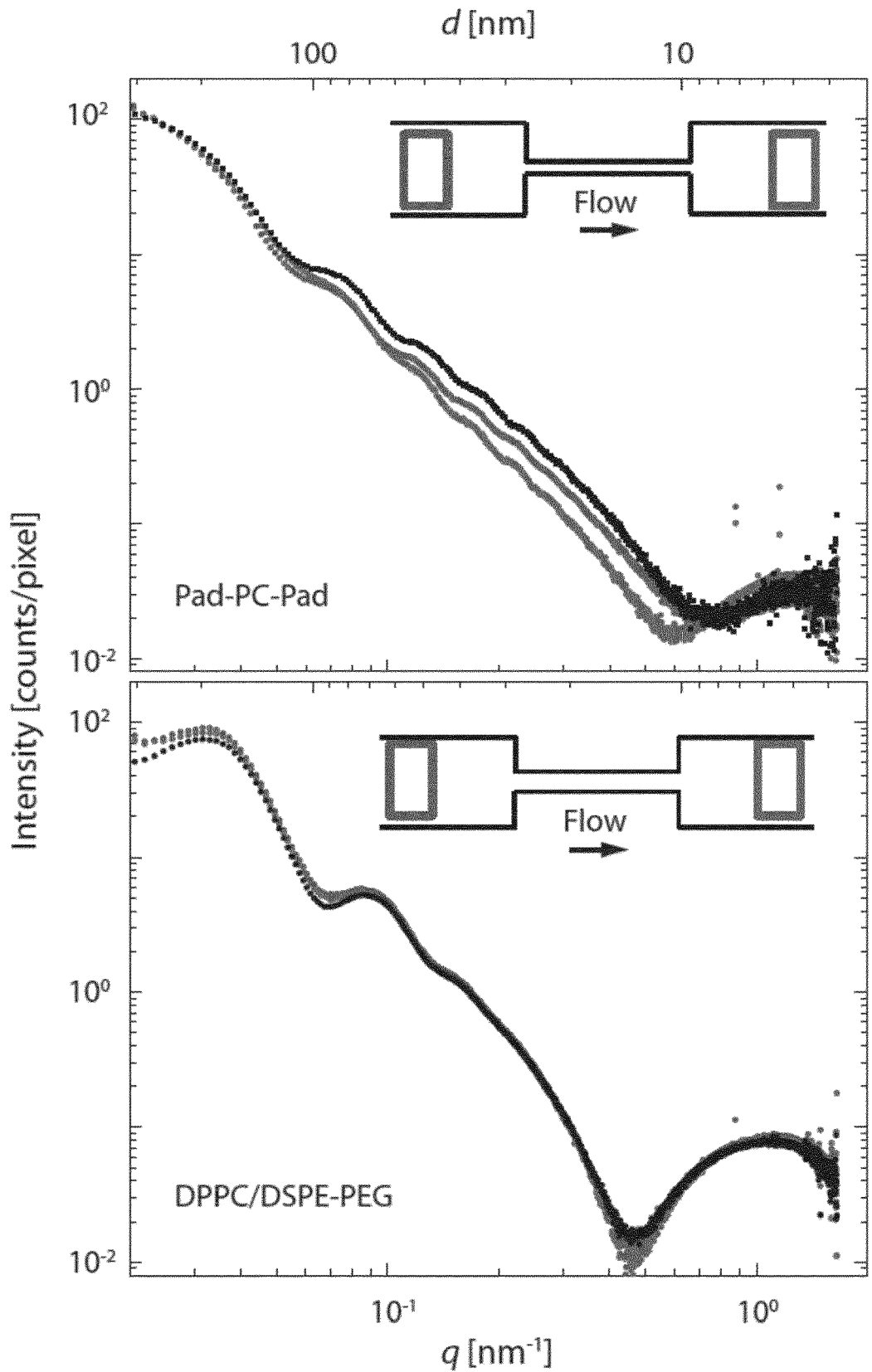
FIG. 15 Comparison of the scattering intensity curves for the same maximum shear acting on Pad-PC-Pad (top) and DPPC/DSPE-PEG (bottom) before (blue-colored dots) and after (red-colored dots) constriction. A significant shift of the bilayer peak of Pad-PC-Pad liposomes is observed after the constriction with respect to the scattering signal before the constriction and under static condition (dark-colored dots).

The response of Pad-PC-Pad liposomes to the flow field was compared to the one of DPPC/DSPE-PEG as reported in FIG. 15. Herein, the scattering signals of Pad-PC-Pad and DPPC/DSPE-PEG were radially integrated in the two areas—blue and red boxes—indicated in the device sketches of FIG. 15.

DPPC/DSPE-PEG measurements in dynamic condition were carried out in a microfluidic device having a constriction width two times wider ($w_{constriction}$=250 μm) than the one utilized for Pad-Pad-Pad. For a fair comparison, and considering Eq. 1, the same shear condition at the constriction location was obtained by setting twice the flow rate for DPPC/DSPE-PEG liposomes than the flow rate to which Pad-PC-Pad liposomes were subjected.

Whereas significant differences in scattering curves, including the shift of the bilayer peak, from the SAXS signals Pad-PC-Pad liposomes before and after the constriction are present, no changes of DPPC/DSPE-PEG liposomes could be probed, as their scattering signals under static condition and under dynamic condition (before and after the constriction) overlapped.

The comparison with DPPC/DSPE-PEG liposomes supports the inventors' hypothesis that Pad-PCPad liposomes are mechano-responsive, already before the constriction and at the shear rates here investigated.

TABLE 3

Pad-PC-Pad liposomes head-to-head distance dhh under static condition (glass capillary) and under dynamic condition in the seven regions (see sketch of FIG. 13) of the microfluidic device. The data represent the mean values of the normal distribution, including the associated errors derived from the standard deviation.

| | | $d_{hh}$ [rim] | | | | | | |
|---|---|---|---|---|---|---|---|---|
| flow rate | glass | microfluidic device positions | | | | | | |
| [pL/s] | capillary | #1 | #2 | A | #$^3$ | B | #4 | #$^5$ |
| 0 | 3.3 ± 0.8 | | | | | | | |
| 0.002 | | 3.4 ± 0.7 | 3.1 ± 0.4 | 3.4 ± 0.5 | 3.9 ± 0.7 | 4.0 ± 0.6 | 3.9 ± 0.4 | 3.8 ± 0.3 |
| 0.02 | | 3.4 ± 0.7 | 2.9 ± 0.2 | 2.9 ± 0.2 | 3.5 ± 0.6 | 4.3 ± 0.5 | 3.6 ± 0.3 | 3.9 ± 0.4 |
| 0.20 | | 3.4 ± 0.9 | 3.4 ± 0.7 | 3.2 ± 0.6 | 3.8 ± 0.8 | 4.4 ± 0.4 | 4.0 ± 0.6 | 4.0 ± 0.7 |

TABLE 4

Radius of gyration Rg of Pad-PC-Pad liposomes under static condition (glass capillary) and under dynamic condition as a function the microfluidic device positions displayed in the sketch of FIG. 13. The data represent the mean values of the normal distribution, including the associated errors derived from the standard deviation.

| | | $R_g$ [nm] | | | | | | |
|---|---|---|---|---|---|---|---|---|
| | | microfluidic device positions | | | | | | |
| [pL/s] | capillary | #$^1$ | #2 | A | #$^3$ | B | #4 | #$^5$ |
| 0 | 60.3 ± 0.4 | | | | | | | |
| 0.002 | | 59.5 ± 0.2 | 59.1 ± 0.1 | 60.3 ± 0.4 | 63.0 ± 0.5 | 59.3 ± 0.9 | 61.1 ± 0.2 | 61.6 ± 0.2 |
| 0.02 | | 60.2 ± 0.2 | 58.0 ± 0.4 | 55.1 ± 0.5 | 64.3 ± 0.6 | 52.4 ± 0.8 | 59.1 ± 0.3 | 61.3 ± 0.1 |
| 0.20 | | 61.6 ± 0.4 | 61.0 ± 0.5 | 61.4 ± 0.6 | 64.0 ± 0.8 | 52.3 ± 0.9 | 58.0 ± 0.3 | 60.0 ± 0.4 |

Liposome Characterisation by Dynamic Light Scattering

A library of artificial phospholipids was synthesised. Table 5 summarises the characterisation of the liposomal formulations concerning hydrodynamic size and polydispersity, before and after the temperature-dependent SANS measurements. The size of the DPPC and Pad-PC-Pad liposomes was (120±2) nm with a polydispersity index between 0.01 and 0.20. Rad-PC-Rad, Pes-PC-Pes, and Sad-PC-Sad liposomal formulations showed a mean size of 150 to 170 nm with a polydispersity index of 0.57 and 0.23. Pad-Pad-PC and Sur-PC-Sur liposomes were 400 to 1,500 nm in size with a polydispersity index of 0.57. In the course of the SANS experiments, the liposomes underwent heating to 42° C. and back to room temperature, which resulted in substantial changes of hydrodynamic sizes and the polydispersity indices. In general, the liposomes showed an increase in size. The only exception was found for Pad-PC-Pad liposomes, which exhibited a decrease by a factor of two. This result for the DLS measurements was confirmed using cryo-TEM.

Small-Angle Neutron Scattering Measurements

The SANS experiment covers the entire nanometer range, because the q-range from 0.01 to 3 $nm^{-1}$ corresponds to real-space periodicities between 2 and 600 nm. Therefore, we were able to determine not only the liposomes' sizes, but also their lipid bilayer thickness. Radius and the eccentricity were calculated only for Pad-PC-Pad liposomes.

Figure 16:
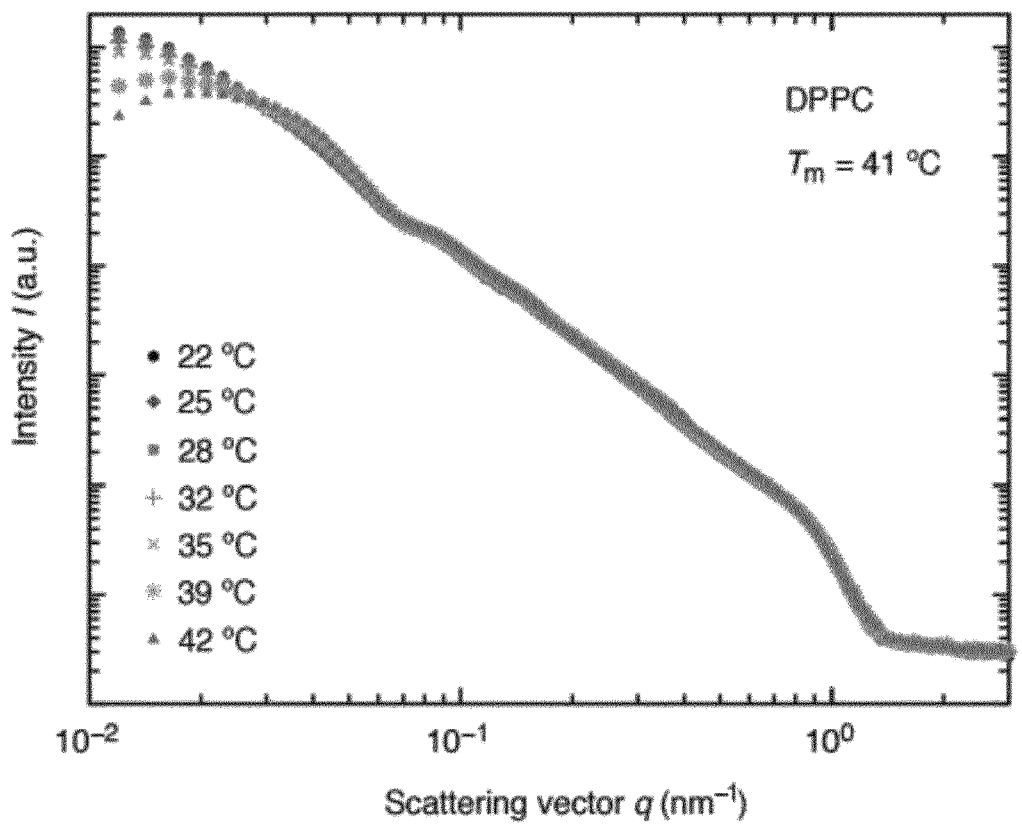
FIG. 16 SANS data q-plots for the DPPC liposomes showed only minor differences for the selected temperatures. The scattering signal before (filled dots) and after (open circles) the heating cycles is almost identical. The cryo-TEM image obtained after the SANS measurement displays faceted liposomes with a size of around 100 nm, while the scale bar corresponds to 100 nm.
Figure 16:
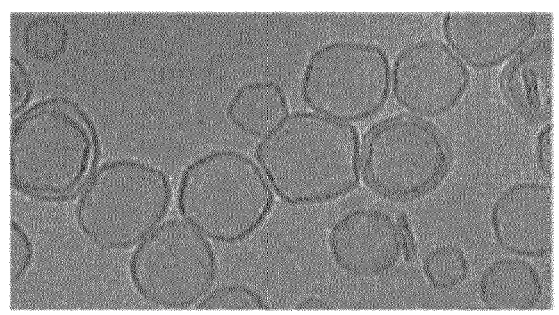
Figure 16:
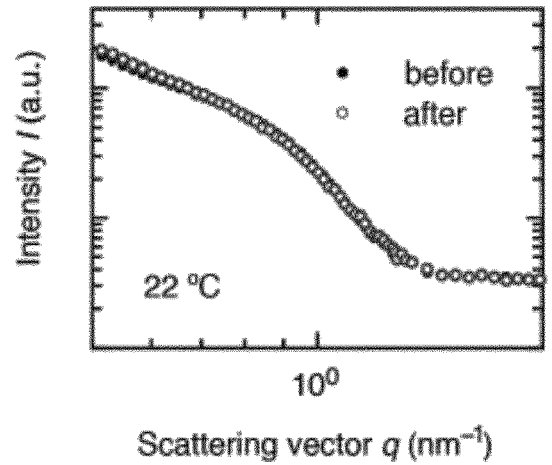

FIG. 16 shows the q-plots of DPPC liposomes for the selected temperatures. The scattering curves are very similar and only differ for the low q-range, where intensity decreases in line with increasing temperature. Note that these changes are especially obvious between 35 and 39° C. and are associated with the pre-transition temperature of DPPC liposomes that varies between 33.5° C.[29] and 35.8° C., which is even higher—37.4° C. in case of the use of $D_2O$. No difference in bilayer thickness could be observed before or after heating, as indicated by the overlapping curve in the bottom-right diagram.

The mean size of the DPPC liposomes, as derived from cryo-TEM images and represented exemplarily in FIG. 16, was found to be (87±20) nm, which is seven to eight times smaller than the average diameter derived from DLS. The inventors attribute this difference to liposome clustering, due to the heat treatment and eight months' storage. About 16% of the liposomes were multi-lamellar, as determined by cryo-TEM.

Figure 17:
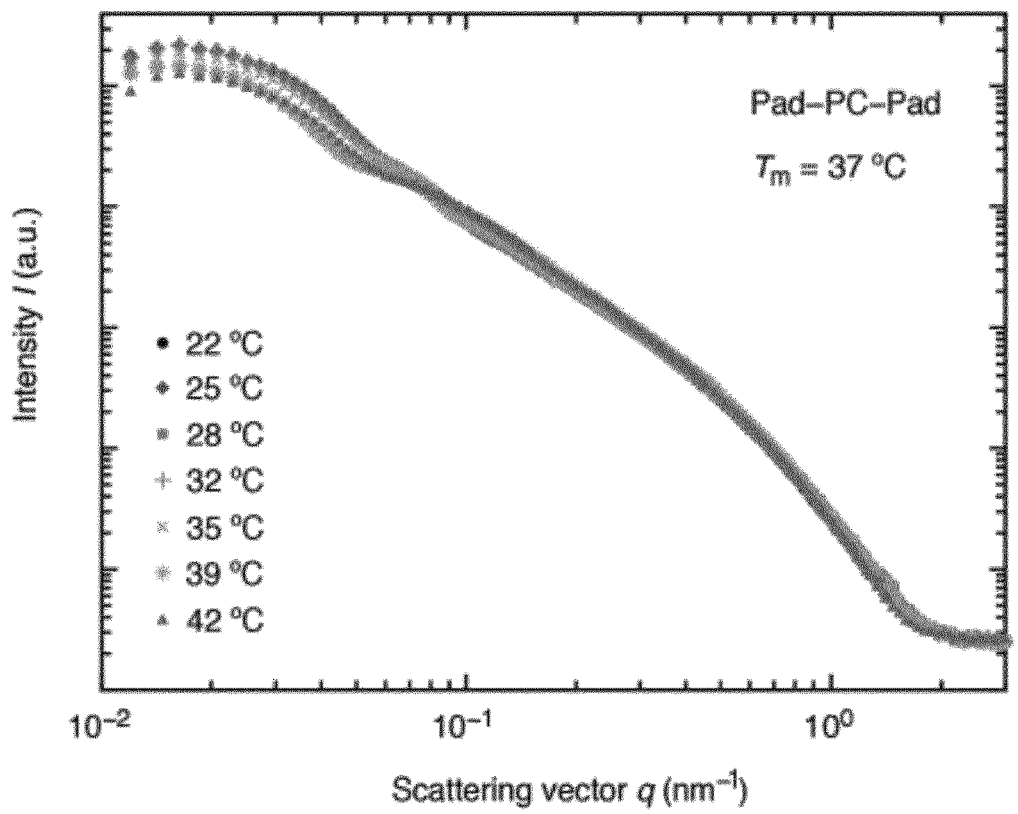
FIG. 17 SANS data q-plots for the Pad-PC-Pad liposomes, which were obtained below and above the transition temperature $T_m$, reveal temperature-dependent structural changes along the entire nanometer range. As shown by the graphs in the second diagram, heating during the SANS experiments induced structural changes corresponding to bilayer thickness periodicity. The two selected parts of the cryo-TEM micrographs, recorded after and before the SANS measurements, are characteristic of the structural changes to the liposomal formulation. The scale bars have a length of 100 nm.
Figure 17:
Figure 17:
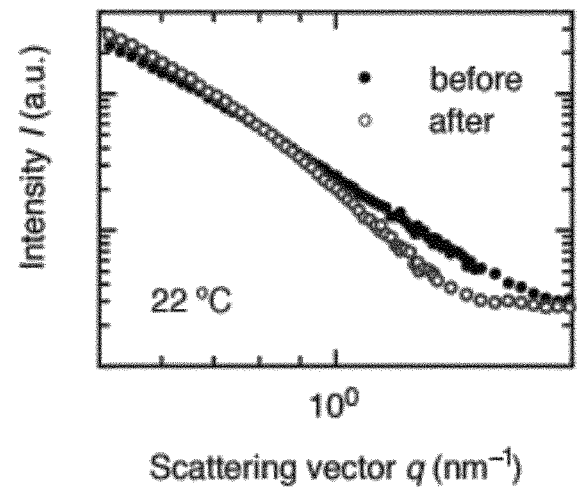

FIG. 17 comprises the q-plot series for the Pad-PC-Pad liposomes. Along with increasing temperature, the intensity of the low-q range reduces by almost a factor of two, thereby indicating liposome division. This disintegration of the Pad-PC-Pad liposomes is in line with the DLS measurements (see Table 5).

The micrograph on the left is a cryo-TEM image of Pad-PC-Pad liposomes heated above $T_m$. It reveals the presence of numerous flattened liposomes and/or bicelles with a diameter of about 50 nm. Pad-PC-Pad liposomes prepared in an identical way, but not heated above their transition temperature, were much larger and encompassed a far greater volume, as verified by the cryo-TEM image in FIG. 17 on the right. The average size of these Pad-PC-Pad liposomes was estimated from cryo-TEM images at (92±14) nm, which is 25% smaller than the value derived from DLS, as illustrated in Table 5. The higher value detected by DLS could have been caused by liposomes clustering as well.

The q-plot also features a shift at low q-values related to bilayer thickness. The diagram on the right of FIG. 17 shows clearly the non-reversible bilayer thickness increase. The temperature increase above $T_m$ and the subsequent cooling to room temperature cause the loss of interdigitation.

Figure 18:
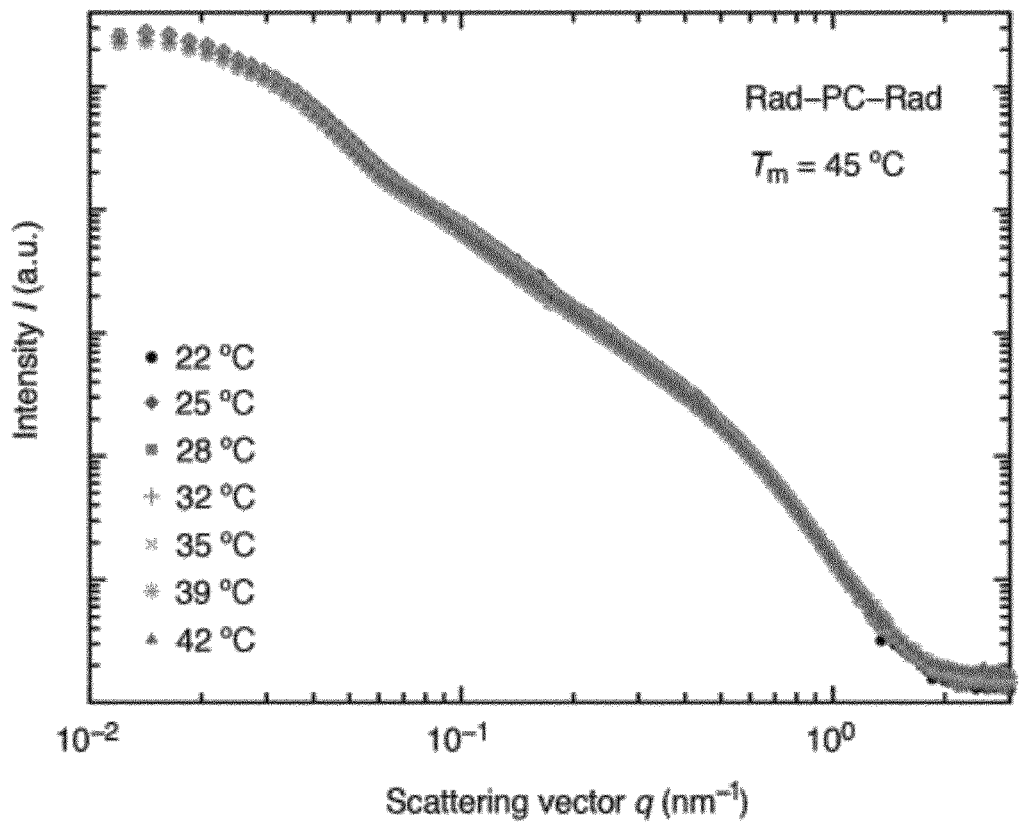
FIG. 18 The SANS scattering signal of Rad-PC-Rad liposomes is almost identical for the temperature range investigated. The liposomes, seen in the cryo-TEM images recorded after the SANS measurement, were larger than the 100 nm-long scale bar.
Figure 18:
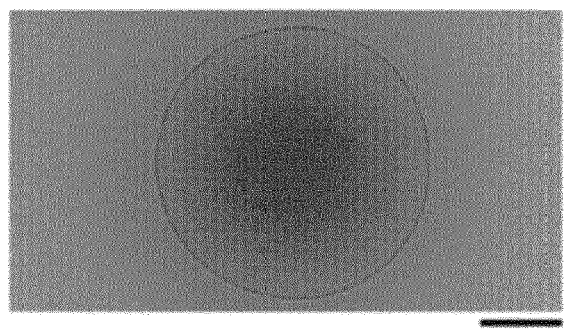
Figure 18:
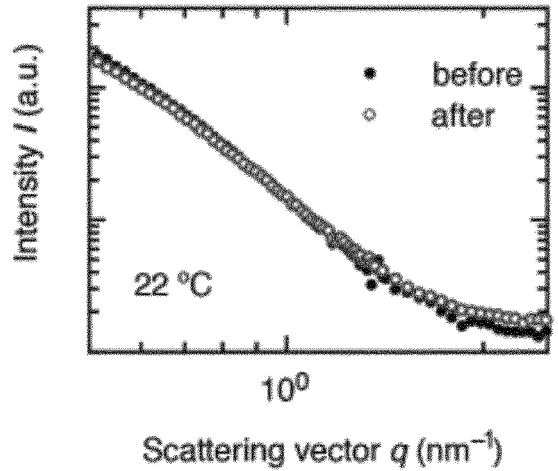

The q-plots obtained from the Rad-PC-Rad liposomes are displayed in FIG. 18. As expected, the increase in temperature to 42° C. did not lead to remarkable changes, because the transition temperature $T_m$=45° C. lies outside the investigated range.

The cryo-TEM image section in FIG. 18 only displays one spherical liposome, but the suspension was polydisperse. The cryo-TEM micrographs demonstrate that besides the spherical liposomes, the inventors found faceted, uni- and multi-lamellar liposomes. The DLS data exhibited a dominant peak for liposomes with a dimension of about 150 nm, but liposomes as large as 5 µm could be identified as well.

Figure 19:
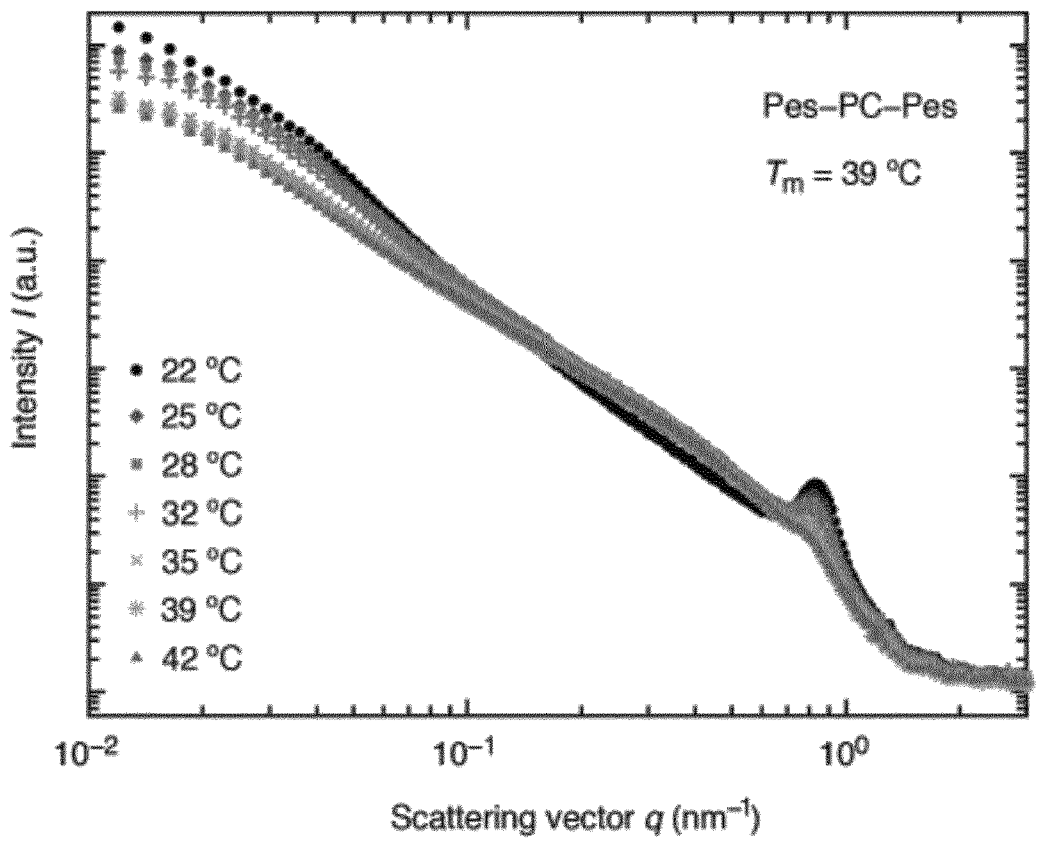
FIG. 19 By increasing the temperature, the neutron scattering signal of Pes-PC-Pes liposomes was substantially altered. After the heating cycle, the peak at q=0.83 nm$^{-1}$ almost disappeared. The cryo-TEM micrograph shows characteristic structures with sizes well above the length of the 100 nm-long bar.
Figure 19:
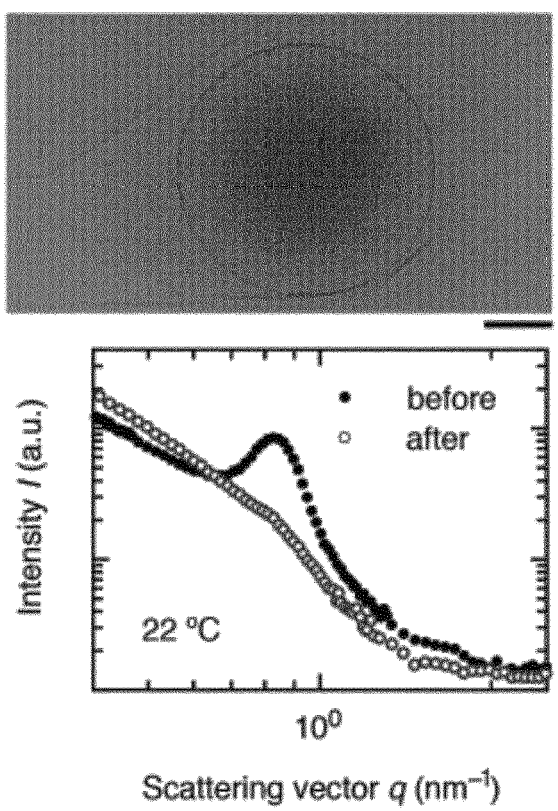

In the case of Pes-PC-Pes liposomes, the increase in temperature from 22 to 42° C. gave rise to fundamental changes in the neutron scattering signal, as outlined in FIG. 19. For the low q-values, one does not find a plateau, as known from nanometer-size liposomes, and because the DLS measurements exhibit the presence of two liposome populations with sizes of about 100 nm and 1 µm, the absence of the plateau indicates the presence of giant liposomes, which the present SANS setup cannot resolve.

The prominent Bragg peak at q=0.83 $nm^{-1}$ results from the presence of stacked lipid bilayers. On increasing the temperature, the peak gradually diminishes, and so one can therefore conclude that liposomes with stacked lipid layers disintegrate at elevated temperatures. The diagram on the right of FIG. 19 shows the irreversibility of the process.

The cryo-TEM micrographs of Pes-PC-Pes are in accordance with such a description. The picture detail of the cryo-TEM data in FIG. 19 shows a representative liposome.

Figure 20:
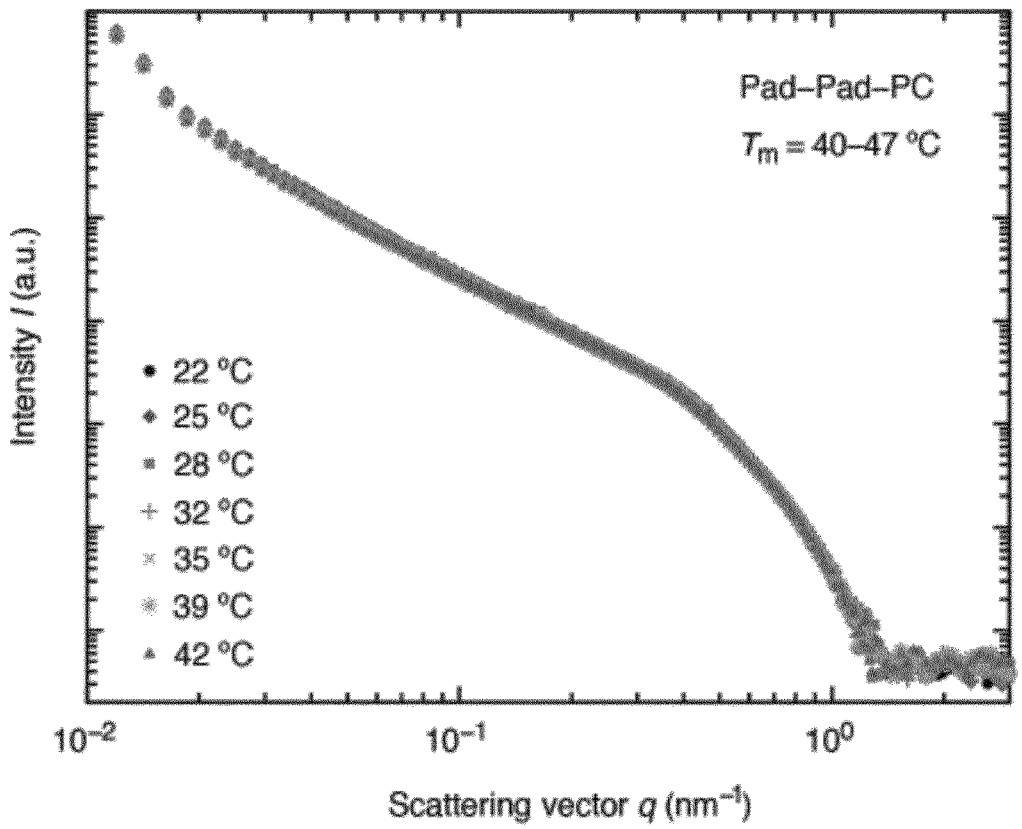
FIG. 20 The q-plots of Pad-Pad-PC liposomes are identical within the temperature range between 22 and 42° C. The suspension contains liposome factors larger than the 100-nm-long scale bar.
Figure 20:
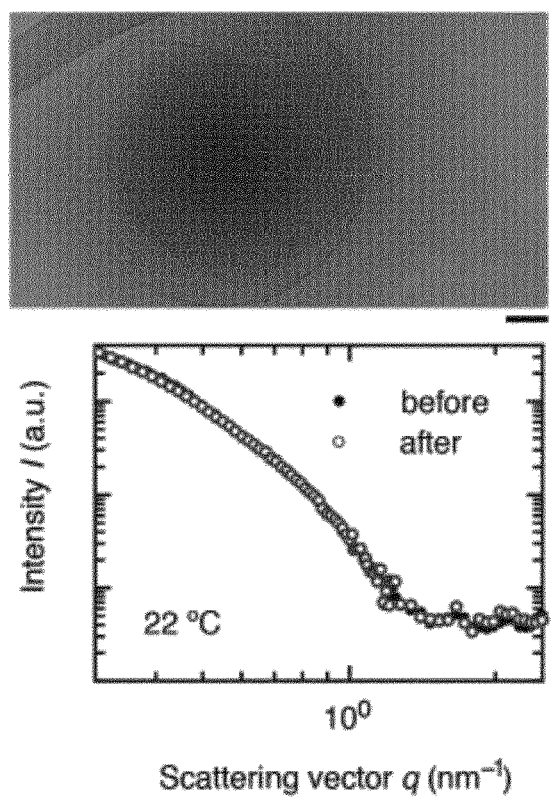

FIG. 20 depicts the unchanged q-plots for the Pad-Pad-PC liposomes in the temperature range investigated herein. Again, the missing plateau at low q-values indicates the presence of micrometer-size liposomes, in agreement with the cryo-TEM micrographs. Many aggregates exhibit sub-units consisting of nanometer-size liposomes, and this observation also agrees with the bimodal size distribution detected by means of DLS. Here, the inventors found a population peaked at sizes of about 150 nm and another one peaked at 3 µm.

Figure 21:
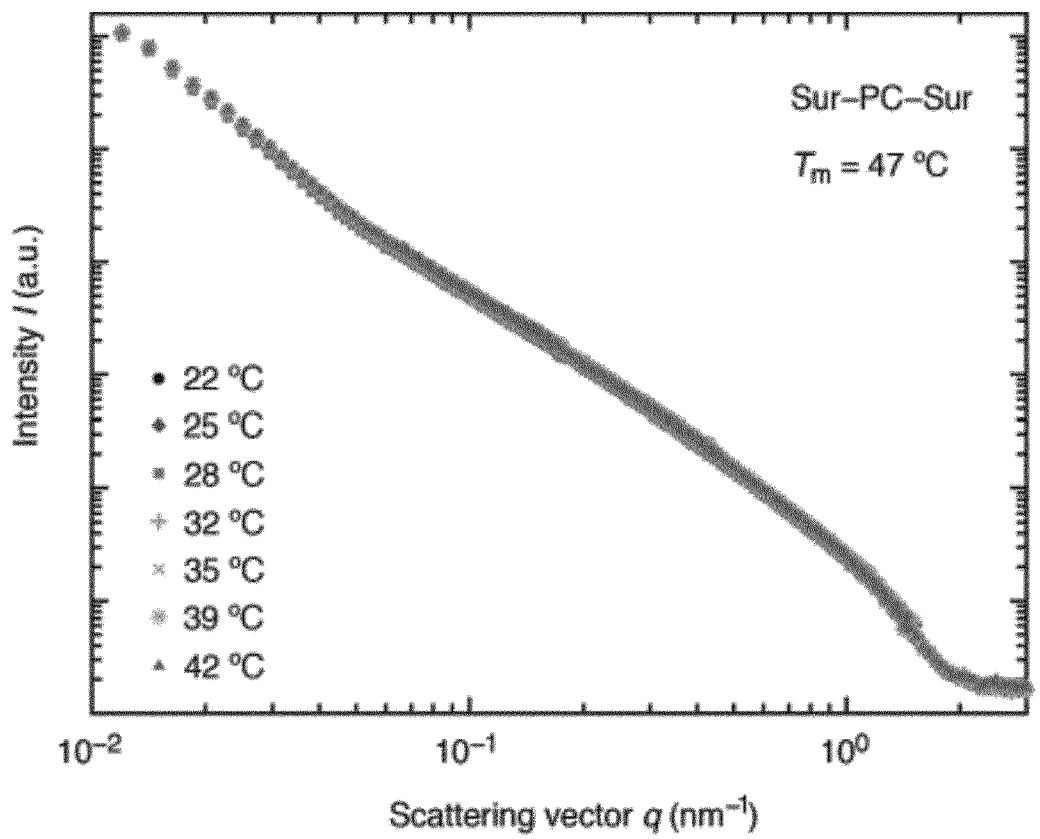
FIG. 21 The q-plots of Sur-PC-Sur liposomes remain constant within the temperature range investigated. The liposomal suspension is inhomogeneous, as one can recognise from the selected cryo-TEM image section. The length bar corresponds to 100 nm.
Figure 21:
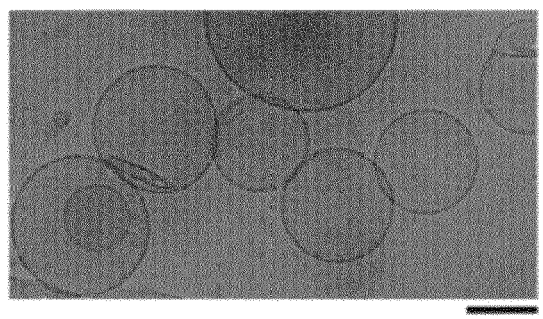
Figure 21:
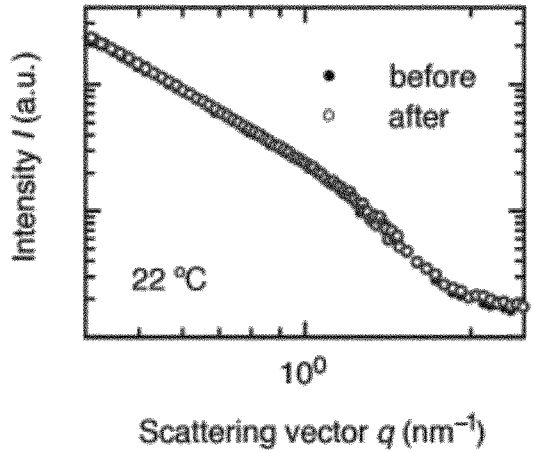

FIG. 21 contains the q-plots of Sur-PC-Sur liposomes within the physiologically relevant temperature range. As hallmarked in the cryo-TEM data, the absence of the plateau seems to be a result of the widespread size distribution, as supported by the DLS data showing bimodal size distribution with liposomes in the micrometre range. The in-homogeneously aggregated liposomes are stable within the temperature range studied.

Figure 22:
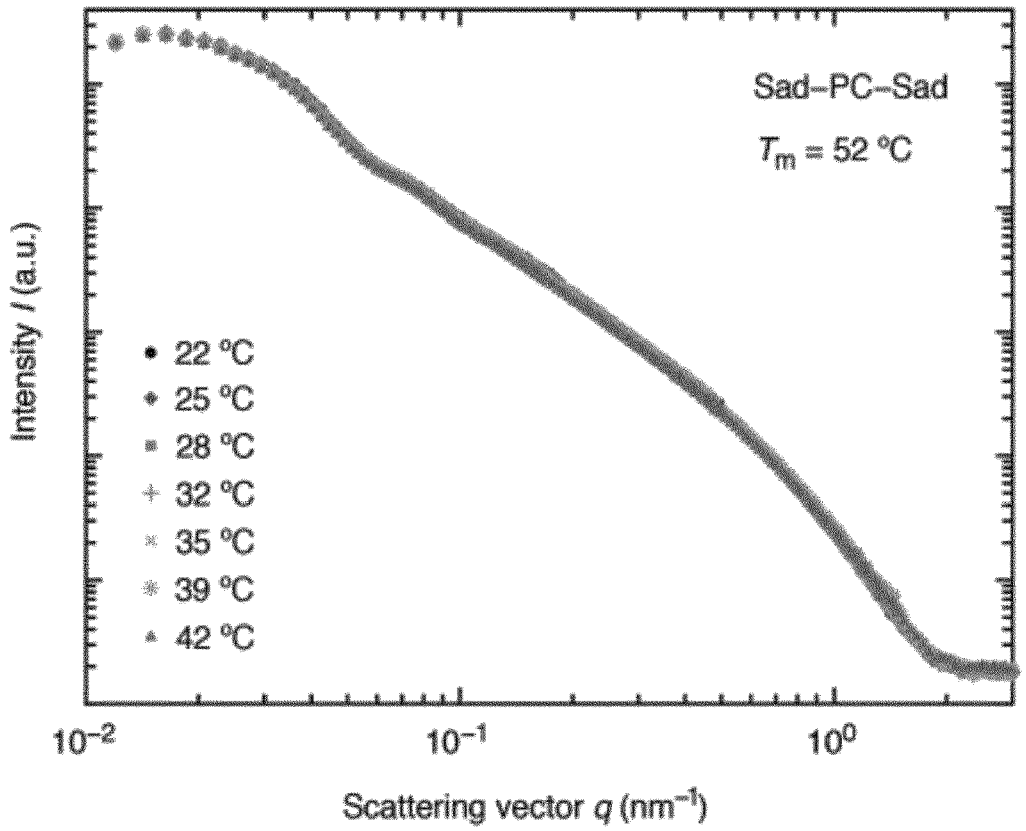
FIG. 22 Within the temperature range considered for the present study, the q-plots hardly change, which means the Sad-PC-Sad liposomes are structurally stable. The cryo-TEM images recorded after SANS measurement show liposomes of various shapes and sizes, but the mean size is in the range of the scale bar with a length of 100 nm.
Figure 22:
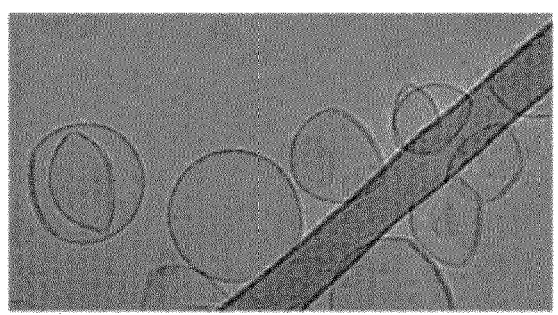
Figure 22:
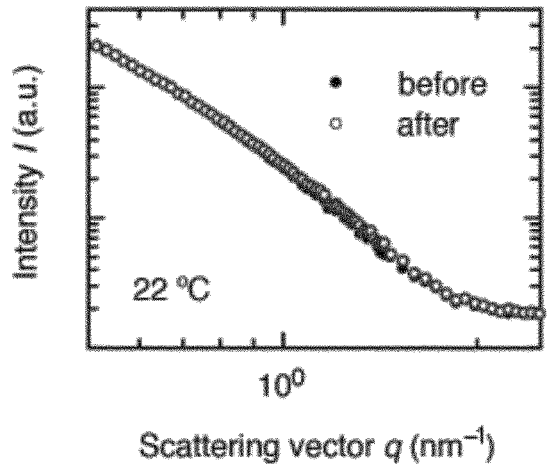

FIG. 22 summarises the results from the Sad-PC-Sad liposomes, and the q-plot has the shape expected for conventional liposomes. Moreover, since the transition temperature is well above the temperature range considered, the curves resemble each other closely.

The cryo-TEM experiments revealed the presence of spherical and non-spherical liposomes, which exhibit several sizes (see section image in FIG. 22). The most probable size derived from DLS was 160 nm, which is in agreement with the cryo-TEM data.

Figure 23:
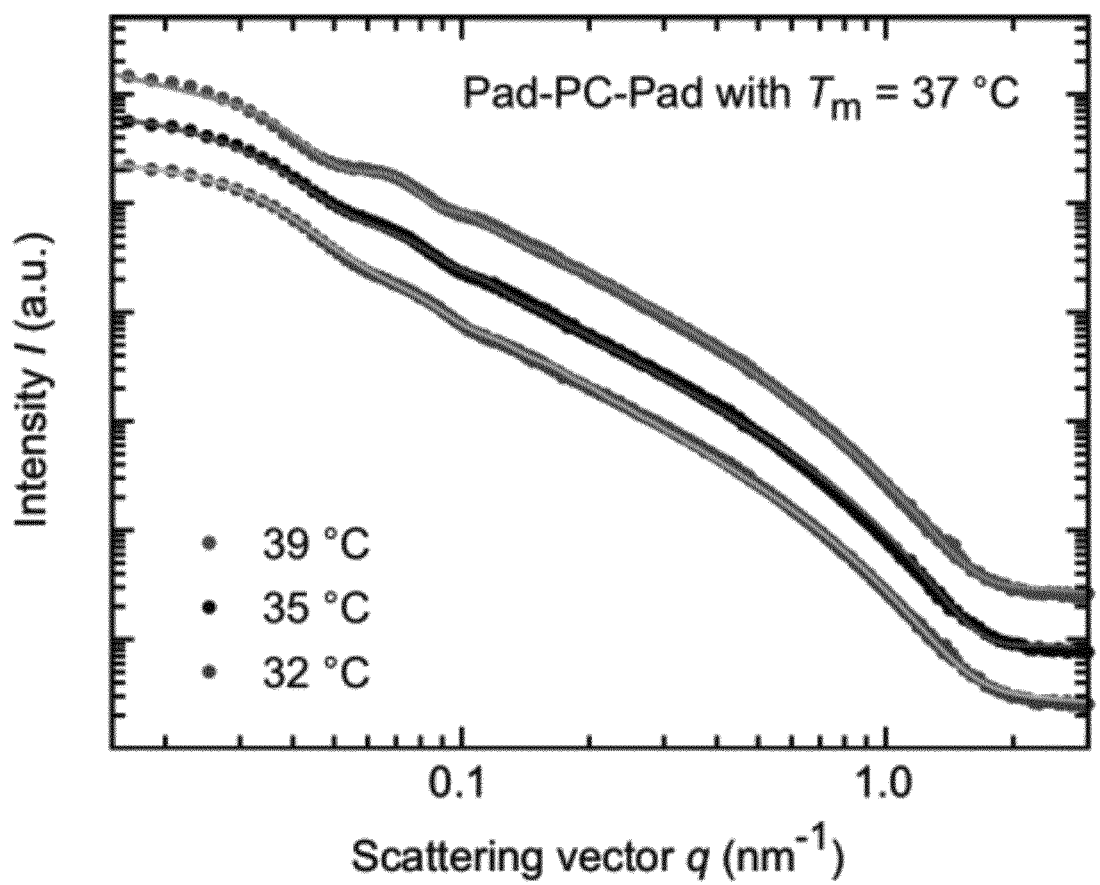
FIG. 23 The diagram specifies how far the selected model (coloured lines) can approximate the experimental neutron scattering data for three selected temperatures (coloured dots). To visualise the differences better, the results for 35 and 39° C. were shifted with respect to those for 32° C. along the ordinate by a factor of three and ten, respectively.

In order to determine the structural parameters, including the bilayer thickness of the selected liposomal formulations, a suitable model for data fitting has to be identified. Herein, for Pad-PC-Pad, the inventors fitted the q-plots using an approach resting upon multiplying the structure factor with the size-averaged form factor, aligned with the assumption that the interaction potential between the liposomes exhibits spherical symmetry and is independent of liposome size. The structure factor was fitted using the sticky hard sphere model (Baxter et al., The Journal of Chemical Physics 1968, 49 (6), 2770-2774; Mays, Langmuir 1989, 5, 422-428). In order to adjust the form factor to the overall shape of the liposomes, an ellipsoidal shell model with a homogeneous cross-section (Guinier, Annales de Physique, 1939; pp 161-237) was applied. The elliptical shell model is defined by three orthogonal axes with lengths a=R, b=R and c=εR, along with eccentricity ε>0, (ε<1: oblate, ε=1: spherical, ε>1: prolate). The model also accounts for variations in bilayer thickness and liposome size. As the scattering data of the Pad-PC-Pad liposomes at the temperature of 35° C. could not be approximated satisfactorily by means of the ellipsoidal shell, the inventors included disks with a homogeneous cross-section—an approach motivated by the cryo-TEM results. Together with the experimental data of the Pad-PC-Pad liposomes at three selected temperatures, the obtained fits are represented in FIG. 23.

Table 6 lists the results of curve fitting for the Pad-PC-Pad liposomes at the temperatures applied in the current study. The fitted values for the liposomes' radii and the thickness of the phospholipid bilayer were constant within the error bars given by the standard deviation. There is, however, a decrease in liposome eccentricity by one order of magnitude, when comparing the data above and below $T_m$. The Pad-PC-Pad liposomes change their shape from faceted to flattened disk-like entities, in accordance with the DLS and cryo-TEM data.

The inventors recognised that the inhomogeneity of the liposomal formulations, except for Pad-PC-Pad, concerning the shape and size of the artificial lipids in this study only allows for the reasonable fitting of the q-range, which corresponds to bilayer thickness. For this purpose, the inventors applied an extended Guinier law (Hjelm et al., The Journal of Physical Chemistry B 2000, 104 (2), 197-211; Fratzl, Journal of Statistical Physics 1994, 77 (1-2), 125-143), which yields the thickness of the bilayer. To account for possible multi-lamellarity, the inventors included a paracrystalline stacking model (Schwartz et al., Biophysical journal 1975, 15 (12), 1201-1233; FruËhwirth et al., Journal of Applied Crystallography 2004, 37 (5), 703-710) as a structure factor. Table 7 illustrates the results of the fits.

Unsurprisingly, DPPC liposomes showed temperature-independent bilayer thickness, although clustering of the liposomes in the course of the thermal cycle was observed. The same applied for the Sur-PC-Sur, Pad-Pad-PC and Rad-PC-Rad liposomes, which also exhibited an almost constant bilayer thickness for the temperatures studied, a behaviour coherent with the phase transition temperatures. The phase transition temperature for Sad-PC-Sad is also above the maximal temperature used for thermal treatment, and so consequently, bilayer thickness variations stayed within the 10% band. For Pes-PC-Pes, however, the transition temperature was in the range examined. In addition, the temperature cycle, including cooling to room temperature, provoked an increase in bilayer thickness of 24%, respectively.

TABLE 5

Results of the dynamic light scattering measurements on liposome formulations used in this study. The main phase transition temperatures ($T_m$) have been reported previously. The hydrodynamic size and the polydispersity index (PDI) were analysed before (n = 5) and after (n = 3) the SANS experiments. Errors correspond to the standard deviation from the independent measurements.

| | | Before heating | | After heating | |
|---|---|---|---|---|---|
| Lipid | $T_m$, ° C. | Size, nm | PDI | Size, nm | PDI |
| DPPC (1) | 41 | 120 ± 2 | 0.01 ± 0.01 | 600 ± 40 | 0.33 ± 0.02 |
| Pad-PC-Pad (4) | 37 | 126 ± 4 | 0.19 ± 0.04 | 53 ± 4 | 0.33 ± 0.04 |
| Rad-PC-Rad (5) | 45 | 150 ± 3 | 0.57 ± 0.01 | 700 ± 100 | 0.32 ± 0.03 |
| Pes-PC-Pes (3) | 39 | 170 ± 20 | 0.57 ± 0.01 | 3100 ± 200 | 0.92 ± 0.08 |
| Pad-Pad-PC (2) | 40-47 | 1500 ± 30 | 0.57 ± 0.01 | n.a. | n.a. |
| Sur-PC-Sur (7) | 47 | 400 ± 100 | 0.57 ± 0.01 | n.a. | n.a. |
| Sad-PC-Sad (6) | 52 | 160 ± 3 | 0.23 ± 0.01 | 220 ± 10 | 0.20 ± 0.02 |

Here, "n.a." means the data could not be extracted because of the aggregate size

TABLE 6

For Pad-PC-Pad the mean radius and bilayer thickness, together with their standard deviations and derived eccentricity, are given. At 35° C., the contribution for disks with homogeneous cross-section was accounted for.

| Temperature, ° C. | Radius, nm | Eccentricity | Bilayer thickness, nm |
|---|---|---|---|
| 22 | 69.96 ± 19.05 | 0.35 | 3.46 ± 1.07 |
| 25 | 66.22 ± 21.15 | 0.35 | 3.38 ± 0.94 |
| 28 | 69.96 ± 16.31 | 0.32 | 3.34 ± 0.91 |
| 32 | 69.90 ± 15.93 | 0.31 | 3.37 ± 0.89 |
| 35 | 64.91 | 0.88 | 3.42 ± 0.88 |
| 39 | 71.96 ± 5.40 | 0.04 | 3.37 ± 0.76 |
| 42 | 71.35 ± 5.01 | 0.05 | 3.57 ± 0.74 |
| 22 | 70.41 ± 31.77 | 0.04 | 4.18 ± 0.70 |

TABLE 7

The most probable bilayer thickness of the liposomes as a function of temperature.

| Phospholipid | Temperature, °C. | | | | | | | |
|---|---|---|---|---|---|---|---|---|
| | 22 | 25 | 28 | 32 | 35 | 39 | 42 | 22 |
| DPPC | 4.59 | 4.58 | 4.62 | 4.61 | 4.61 | 4.65 | 4.65 | 4.67 |
| Rad-PC-Rad | 4.55 | 4.57 | 4.55 | 4.51 | 4.45 | 4.35 | 4.40 | 4.45 |
| Pad-Pad-PC | 5.57 | 5.55 | 5.55 | 5.52 | 5.54 | 5.58 | 5.57 | 5.67 |
| Pes-PC-Pes | 3.90 | 4.17 | 4.46 | 4.42 | 4.60 | 4.68 | 4.58 | 4.82 |
| Sur-PC-Sur | 3.11 | 3.06 | 3.11 | 3.08 | 3.08 | 3.11 | 3.10 | 3.10 |
| Sad-PC-Sad | 3.15 | 3.51 | 3.51 | 3.49 | 3.46 | 3.38 | 3.33 | 3.01 |

Materials and Methods
Liposomes Preparation

Two phospholipids, the commercially available natural 1,2-dipalmitoyl-sn-glycero-3-phosphatidylcholine (DPPC) with 5% molar DSPE-PEG2000 (Lipoid, Zug, Switzerland) and the 1,3-palmitoyl-amido-1,3-deoxy-sn-glycero-2-phosphatidylcholine (Pad-PC-Pad) synthesized according to the recently reported protocol, (Fedotenko et al., Tetrahedron Letters 2010, 51, 5382-5384) were used to prepare liposomes. Briefly, the liposomes were formulated via the standard thin-film method (Walde et al., Encycl. Nanosci. Nanotechnol. 2004, 9, 43-79; Olson et al., Biochimica et Biophysica Acta (BBA)—Biomembranes 1979, 557, 9-23) and hydrated with ultrapure water. Each suspension obtained has a lipid content of 20 mg/mL, which corresponds to the highest concentration achievable using Pad-PC-Pad. The suspensions were freeze-thawed in a twelve-step series of liquid nitrogen cooling and water bath heating (60° C.). To obtain liposomes with a diameter of about 100 nm with a narrow size distribution, multiple barrel extrusions using Liposofast LF-50 (Avestin Inc., Canada) through track-edged polycarbonate_Iter membranes (Whatman Nucleopore, Sigma-Aldrich, Buchs, Switzerland) were applied.

The pore sizes were reduced from 400 nm (five times) via 200 nm (five times) to 100 nm (15 times).

Liposomes Characterization

The lipid concentration of the two formulations was determined using the phosphate test (Stalder and Zumbuehl. CHIMIA International Journal for Chemistry 2013, 67, 819-821). Size and size distribution of the liposomes were quantified by means of dynamic light scattering (DLS) using a Delsa Nano C (Beckman Coulter, USA). DLS measurements were performed at a temperature of 25° C., using two laser diodes working at a wavelength of 658 nm. The scattering angle was set to 165 degrees. Cryo-TEM images of Pad-PC-Pad liposomal suspension were taken by mounting the liposomal suspension on glow-discharged holey carbon grids, quickly frozen by a Cryoplunge CP3 system (Gatan, USA), and transferred to a JEM2200FS transmission electron microscope (JEOL, Japan) using a Gatan626 cryo-holder. Cryo-TEM micrographs were recorded at an acceleration voltage of 200 kV at a magnification of 20,000, 4-8 µm under-focus, and a dose of 10 electrons=$Å^2$, using a F416 CMOS detector (TVIPS, Germany).

Microfluidic Device Fabrication

X-ray compatible microfluidic devices were prepared as reported previously (Lutz-Bueno et al., Lab on a Chip 2016, 16, 4028-403). Briefly, photolithography of SU-8 negative resist (Nano SU-8 100, MicroChem Corp., MA, USA) on Si wafers was used to fabricate the masters. A layer of 250 µm thick photoresist was exposed to UV light through a photo mask with the microfluidic design and was afterwards developed. The microfluidic device design consisted of a horizontal channel of 1000 µm width with a constriction in the middle 2000 µm long. Two designs were realized, with constriction widths of 125 µm and 250 µm. Polydimethylsiloxane (PDMS, Sylgard 184, Dow Corning Corp., Midland, USA) and crosslinker were mixed at a ratio of 10:1 to form flexible replica stamps. The liquid PDMS mixture was poured on the photolithographic master and cured overnight at a temperature of 80° C. Afterwards, the PDMS stamp was peeled off from the master. Norland Optical Adhesive 81 (Norland Products Inc., Cranbury, USA) was poured on a polyimide film of a thickness of 25 µm (Goodfellow Corp., Cambridge, UK). PDMS stamp was placed on the NOA 81 coated polyimide film in order to imprint the microfluidic structure into the NOA 81 coat. After 1 min exposure to UV light, $\lambda=366$ nm, to crosslink NOA 81, the flexible PDMS stamp was peeled off. By using a puncher 0:75 mm in diameter, inlet and outlet holes were obtained. The microfluidic NOA 81/polyimide film was then sealed with a second polyimide film with a thickness of 25 µm.

SAXS Measurements

The spatially resolved SAXS measurements were performed at the cSAXS beamline at the Swiss Light Source (PSI, Villigen, Switzerland). The X-ray beam was focused to 25 µm×50 µm (vertical×horizontal) spot size at the specimen location, the photon energy was set to 11:2 keV ($\lambda=1:1$ Å), and the sample-detector distance to 7:102 m, determined by the first scattering order of a silver behenate specimen. The scattering signal was recorded using the Pilatus 2M detector (Kraft et al., J. Synchrotron Radiat. 2009, 16, 368-375) (pixel size: 172 µm_×172 µm). Dynamic spatially resolved SAXS measurements of the liposomal suspensions were performed using microfluidic devices mounted on an aluminum/polyetheretherketone/aluminum sample holder. Two-dimensional (2D) scans were realized line-by-line by continuously moving the device in horizontal direction, while the detector recorded the data in burst mode. 48 (v)×96 (h) points at step size 25 µm (v)×50 µm (h) were acquired in a pre-selected region of the microfluidic device with an exposure time of 1:5 s per point. The data were processed using the Matlab package available from the beamline (https://www.psi.ch/sls/csaxs/software). During the experiment, the flow rates were adjusted using a syringe pump system (Nemesys, Cetoni GmbH, Korbussen, Germany) connected to the microchannel using polytetrafluoroethylene (PTFE) tubing. For the point-wise background correction, the scattering signal of ultra-pure water in the microfluidic device for all the measured flow rates was recorded before the acquisition of the SAXS signal of the liposomal suspensions. For the microfluidic device with a rectangular channel cross-section, the wall shear rates were calculated from the volumetric flow rates v using the following equation: (Molloy et al., Journal of Thrombosis and Haemostasis 2016, 15, 972-982)

$$\lambda=6v=h^2w \qquad (1)$$

with the shear rate [$s^{-1}$], v the volumetric flow rate [µL/s], and w and h the width and height [µm] of the channel, respectively.

In addition, static SAXS measurements of the two liposomal suspensions and the ultra-pure water were carried out in boron silicate glass capillaries (Hilgenberg, Malsfeld, Germany) having an outer diameter of 1.5 mm and wall thickness of 0.01 mm using the parameters given above.

Liposome Preparation for SANS

Lipids were formulated according to the protocols previously reported (Holme et al., Nature Nanotechnology 2012, 7 (8), 536-543; Neuhaus et al., Langmuir 2018, 34 (10), 3215-3220; Neuhaus et al., Soft matter 2018, 14 (19), 3978-3986; Neuhaus et al., Angewandte Chemie 2017, 129 (23), 6615-6618), while liposomes were prepared following the standard extrusion protocol (Holme et al., Nature Nanotechnology 2012, 7 (8), 536-543). In summary, 10 mg of lipids were dissolved in $CH_2Cl_2$. After evaporating the organic solvent, the thin film was dried further under vacuum conditions (40 mbar) overnight. The film was hydrated with $D_2O$ for a period of 30 minutes. Five freeze-thaw cycles (liquid $N_2$ to 65° C. water bath) were carried out and followed by eleven extrusion cycles, using a Mini Extruder (Avanti Polar Lipids, USA) and track-edged filters with a 100 nm pore size (Whatman, USA). The obtained liposomal formulations exhibited a lipid concentration of about 10 mg/mL.

Small-Angle Neutron Scattering (SANS)

SANS measurements were performed at the SANS-I beamline at the Swiss Spallation Neutron Source SINQ facility (Paul Scherrer Institute, Villigen, Switzerland). The samples were loaded into 2 mm-path length, boron-free quartz glass cells and mounted in a temperature-controlled holder. This system allows for controlling the temperature of the specimen with an accuracy better than 1 K. The liposomal suspensions were measured between 22 and 42° C. in 3 to 4 K steps. Subsequently, the suspensions were cooled down to room temperature (22° C.) and measured again. Three detector distances, i.e. 1.6, 6.0 and 18.0 m, were used to collect data over the range of scattering vectors $0.01 \text{ nm}^{-1} < q < 10 \text{ nm}^{-1}$ at the neutron wavelengths (A) 0.45 and 1.2 Å. Data were collected with a two-dimensional $^3$He-detector with an array of 128×128 pixels and reduced to one-dimensional I(q) scattering curves, thus radially averaging the two-dimensional images. The data were corrected for transmission, background scattering and detector efficiency according to a standard procedure using the BerSANS software package (Keiderling, Applied Physics A 2002, 74 (1), s1455-s1457; Strunz et al., Journal of Applied Crystallography 2000, 33 (3 Part 1), 829-833).

Cryo-Transmission Electron Microscopy (Cryo-TEM)

The liposomal suspensions were diluted at a ratio of 1:2 with $D_2O$, to a final concentration of 5 mg/mL. Next, 4 µL aliquots of each suspension were adsorbed onto a holey carbon-coated grid (Lacey, Tedpella, USA), blotted with Whatman 1 filter paper and vitrified into liquid ethane at a temperature of −178° C., using a Leica GP plunger (Leica, Austria). Frozen grids were transferred onto a Talos electron microscope (Thermo Fisher, USA), using a Gatan 626 cryo-holder. Electron micrographs were recorded at an accelerating voltage of 200 kV and a nominal magnification of 45,000×, using a low-dose system (20 $e^-/Å^2$) and keeping the sample at liquid nitrogen temperature. Micrographs were recorded on the CETA camera. Pixel size at the sample level was $(3.26 \text{ Å})^2$. Since some of the cryo-TEM micrographs exhibited slowly varying brightness variations, it was compensated for such inhomogeneities by means of a modified fuzzy C-means algorithm (Schulz et al., Sci Rep 2012, 2, 826; Ahmed et al., IEEE Trans Med Imaging 2002, 21 (3), 193-9).

Dynamic Light Scattering (DLS)

DLS measurements were carried out on a DelsaMax PRO (Beckman Coulter, USA) at room temperature and at a lipid concentration of 0.3 mg/mL in $D_2O$. The data were averaged among five independent measurements before heating cycles and three measurements eight months after applying heating cycles. Data were treated with the cumulant analysis method.

Models Used for SANS Data Analysis

The SANS data were analysed using SASfit software (Breßler et al., Journal of Applied Crystallography 2015, 48 (5), 1587-1598) and corresponding models. A Pad-PC-Pad sample was fitted over the entire measured q-range, whereas we restricted the fit for the other samples to the q-range, which corresponds to lipid bilayer thickness. For Pad-PC-Pad, the inventors used an ellipsoidal shell model with a homogeneous cross-section (Guinier, Annales de Physique, 1939; pp 161-237) and size distributions in terms of both thickness and radius. The inventors also included the sticky hard sphere model (Baxter et al., The Journal of Chemical Physics 1968, 49 (6), 2770-2774; Mays, Langmuir 1989, 5, 422-428) to account for inter-particle interactions. For the remaining formulations, the inventors used a generalised Guinier approximation (Hjelm et al., The Journal of Physical Chemistry B 2000, 104 (2), 197-211; Fratzl, Journal of Statistical Physics 1994, 77 (1-2), 125-143) to investigate bilayer thickness, and the inventors also added multi-lamellar contributions (para-crystalline theory) (Schwartz et al., Biophysical journal 1975, 15 (12), 1201-1233; FruÈhwirth et al., Journal of Applied Crystallography 2004, 37 (5), 703-710), where appropriate.

DISCUSSION

Pad-PC-Pad liposomes can reveal a faceted morphology below $T_m$, associated with lipid bilayer interdigitation. Using SAXS, the inter-lamellar spacing of Pad-PC-Pad liposomes was measured and indicated the de-interdigitation of phospholipid chains above $T_m$. SAXS data have revealed that the head-to-head distance of lipid molecules within the Pad-PC-Pad bilayer corresponds to (3.3±0.8) nm. The loss of interdigitation explains the 21% increase in bilayer thickness after the heating cycle. Obviously, cooling did not result in the original state, but the liposomes disintegrated into nanostructures of half their original size measured before the heating cycle. The instability of Pad-PC-Pad liposomes at physiologically relevant temperatures is counter-indicative of its use as a carrier for targeted drug delivery within the human body.

The Rad-PC-Rad phospholipid, as with the C17 homologue of Pad-PC-Pad, features with $T_m$=45° C. a higher transition temperature, which should allow for shear-responsive drug delivery within the human body. The present study confirms that the Rad-PC-Rad liposomes are thermally stable up to 42° C. and do not show any structural change in the physiologically relevant temperature range between 22 and 42° C.

Pes-PC-Pes is also known as the b-DPPC analogue of DPPC. In the gel phase, b-DPPC exhibited a hexagonal chain packing structure and bilayer interdigitation, whereas in the liquid crystalline phase the bilayer chain interdigitation disappeared. Phase transition involves an increase in bilayer thickness by 20%—a value consistent with the present study, where the inventors found an 18% increase in the bilayer thickness of Pes-PC-Pes liposomes.

It is shown that the thermal behaviour of Pad-Pad-PC liposomes is complex and the 1,2-arrangement of the phospholipid prevents membrane interdigitation. As the transition temperature with 46° C. is well above the temperatures studied, it is hardly surprising that the inventors did not detect any structural change, and the same notion applies for the liposomes composed of Sad-PC-Sad and Sur-PC-Sur lipids.

The invention claimed is:
1. A mechanoresponsive vesicle comprising a membrane and a volume limited by said membrane, wherein said membrane comprises 1,3-diheptadecanamidopropan-2-yl (2-(trimethylammonio) ethyl) phosphate, wherein the mechanoresponsive vesicle is thermally stable up to 42° C.
2. The mechanoresponsive vesicle according to claim 1, wherein said membrane is a bilayer structure.
3. The mechanoresponsive vesicle according to claim 2, wherein said bilayer structure comprises an interdigitated phase, and said interdigitated phase is formed within a temperature range of 42° C. to 46° C.
4. The mechanoresponsive vesicle according to claim 1, wherein said mechanoresponsive vesicle comprises a pharmaceutical agent or drug, or a diagnostic agent.
5. The mechanoresponsive vesicle according to claim 4, wherein said pharmaceutical drug or diagnostic agent is selected from the group consisting of:
   a fibrinolytic agent,
   an anti-coagulation agent,
   an anti-aggregation agent,
   an atherosclerotic plaque stabilizer,
   a vasodilatory agent, an alpha-adrenoceptor antagonist, an angiotensin converting enzyme inhibitor, an angiotensin receptor blocker, a direct renin inhibitor, a calcium-channel blocker, an endothelin receptor antagonist, a phosphodiesterase inhibitor, a potassium-channel opener,
   an anti-arrhythmic drug,
   an inotrope positive medication,
   a heart muscle remodeling drug,
   a drug for diastolic dysfunction treatment,
   a drug for decongestion,
   a radio contrast marker,
   a chemotherapeutic agent,
   a coagulation factor agent, and
   an anti-inflammatory agent.
6. The mechanoresponsive vesicle according to claim 4, wherein said pharmaceutical drug or diagnostic agent is selected from the group consisting of alteplasum, heparin, acetyl salicylic acid, clopidogrelum, glycoprotein IIb/IIIa inhibitor, rosuvastatinum, a nitric oxide liberating agent, nitroprusside, molsidomine, phentolamine, enalapril, candesartan, diltiazem, bosentan, milrinone, levosimendan, minoxidilum, aliskirenum, quinidine, metoprolol, amiodarone, verapamil, epinephrine, norepinephrine, dopamine, dobutamine, isoprenalin, levosimendan, vasopressin, glypressin, brain natriuretic peptide, nesiritidum, nitroglycerine, alteplasum, eptacogum alfa, recombinant Factor VII, iodine or an iodine containing contrast agent, a gadolinium containing contrast agent, a cardiomyocyte and a stem cell.
7. The mechanoresponsive vesicle according to claim 6, for use in the treatment of one of:
   a cardio-vascular disease,
   a dermatological disease, or a tumor treatment.
8. The mechanoresponsive vesicle according to claim 7, wherein said cardio-vascular disease is selected from the group consisting of acute coronary syndrome, myocardial infarction, acute heart insufficiency, chronic heart insufficiency, cerebrovascular accident, stroke, atherosclerosis, vasospasm, hemoptysis, pulmonary embolism, pulmonary arterial hypertension, intestinal ischemia, intestinal hemorrhage, renal infarction, renal hemorrhage, renal auto-regulation for hypertensive treatment, auto-immune glomerulonephritis interstitial nephritis, placental infarction, placental hemorrhage, retinal ischemia, retinal hemorrhage, and retinal neovascularization, wherein the mechanoresponsive vesicle is thermally stable up to 42° C.
9. The mechanoresponsive vesicle according to claim 7, wherein said dermatological disease is selected from the group consisting of:
   acne,
   napkin dermatitis,
   atopic dermatitis,
   seborrheic dermatitis,
   psoriasis,
   warts,
   tinea pedis,
   seborrheic keratosis,
   hives,
   rosacea,
   dermatological viral infection, or
   dermatological bacterial infection.
10. A method of preparing a mechanoresponsive vesicle comprising the steps of
   providing 1,3-diheptadecanam idopropan-2-yl(2-(trimethylammonio)ethyl) phosphate dissolved in an organic solvent;
   removing said organic solvent under an inert atmosphere thereby obtaining a lipid sheet;
   solving said lipid sheet in a first aqueous buffer solution having a physiological pH;
   applying at least one freezing step and one thawing step;
   extrusion of said suspension, thereby obtaining an extrudate; and
   dialyzing the extrudate in a second buffer solution having a physiological pH to remove small molecular weight components.
11. The mechanoresponsive vesicle obtained by the method according to claim 10.
12. The mechanoresponsive vesicle prepared by the method according to claim 10 for use in a method of monitoring or diagnosis.
13. The method according to claim 10, wherein said extrusion of said suspension is performed through a filter having a pore diameter in a range of 50 nm to 150 nm.
14. The mechanoresponsive vesicle of claim 1, wherein a spontaneous release rate after 2 hours at 37 degrees Celsius is less than about 54.55%.
15. The mechanoresponsive vesicle of claim 1, wherein a ratio of the release after 60 second vortex at 37 degrees Celsius and a spontaneous release rate at 37 degrees Celsius after 2h is greater than about 5.7.
16. The mechanoresponsive vesicle according to claim 1, wherein the mechanoresponsive vesicle releases its cargo when it is mechanically stimulated.
17. The mechanoresponsive vesicle according to claim 1 for use in a method of monitoring or diagnosis.

* * * * *